(12) United States Patent
Garudadri et al.

(10) Patent No.: US 11,819,343 B2
(45) Date of Patent: *Nov. 21, 2023

(54) WEARABLE SYSTEM FOR CAPTURING AND TRANSMITTING BIOMEDICAL SIGNALS

(71) Applicant: QUALCOMM Incorporated, San Diego, CA (US)

(72) Inventors: Harinath Garudadri, La Jolla, CA (US); Pawan Kumar Baheti, Bangalore (IN)

(73) Assignee: QUALCOMM Incorporated, San Diego, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 17/182,096

(22) Filed: Feb. 22, 2021

(65) Prior Publication Data
US 2021/0169426 A1 Jun. 10, 2021

Related U.S. Application Data

(63) Continuation of application No. 16/227,955, filed on Dec. 20, 2018, now Pat. No. 10,939,873, which is a
(Continued)

(51) Int. Cl.
*A61B 5/00* (2006.01)
*A61B 5/1455* (2006.01)
(Continued)

(52) U.S. Cl.
CPC .......... *A61B 5/7232* (2013.01); *A61B 5/0006* (2013.01); *A61B 5/0024* (2013.01);
(Continued)

(58) Field of Classification Search
CPC ... A61B 5/7232; A61B 5/0006; A61B 5/0024; A61B 5/14551; A61B 5/021;
(Continued)

(56) References Cited

U.S. PATENT DOCUMENTS 4,869,262 A 9/1989 Orr et al.
5,511,553 A 4/1996 Segalowitz
(Continued)

FOREIGN PATENT DOCUMENTS

CN 1550204 A 12/2004
EP 0733340 A1 9/1996
(Continued)

OTHER PUBLICATIONS

English translation of JP2006053845. (Year: 2006).*
(Continued)

*Primary Examiner* — Michael P Nghiem
(74) *Attorney, Agent, or Firm* — QUALCOMM Incorporated

(57) ABSTRACT

Certain aspects of the present disclosure relate to a method for compressed sensing (CS). The CS is a signal processing concept wherein significantly fewer sensor measurements than that suggested by Shannon/Nyquist sampling theorem can be used to recover signals with arbitrarily fine resolution. In this disclosure, the CS framework is applied for sensor signal processing in order to support low power robust sensors and reliable communication in Body Area Networks (BANs) for healthcare and fitness applications.

18 Claims, 31 Drawing Sheets

Related U.S. Application Data continuation of application No. 12/512,480, filed on Jul. 30, 2009, now Pat. No. 10,213,164.

(60) Provisional application No. 61/101,056, filed on Sep. 29, 2008, provisional application No. 61/100,654, filed on Sep. 26, 2008.

(51) Int. Cl.
  *G01R 13/02* (2006.01)
  *H03M 7/30* (2006.01)
  *A61B 5/021* (2006.01)

(52) U.S. Cl.
  CPC ...... *A61B 5/14551* (2013.01); *G01R 13/0272* (2013.01); *H03M 7/30* (2013.01); *A61B 5/021* (2013.01); *A61B 2560/0209* (2013.01); *G06F 2218/00* (2023.01)

(58) Field of Classification Search
  CPC .............. A61B 2560/0209; A61B 5/02; G01R 13/0272; G06K 9/00496; H03M 7/30
  USPC ....................................................... 702/189
  See application file for complete search history.

(56) References Cited

U.S. PATENT DOCUMENTS

| | | | |
|---|---|---|---|
| 5,749,366 A | 5/1998 | Odagiri et al. | |
| 5,961,577 A | 10/1999 | Soenen et al. | |
| 7,018,338 B2 | 3/2006 | Vetter et al. | |
| 7,091,894 B2 * | 8/2006 | Fudge ................. | H03M 1/0626 341/120 |
| 7,297,119 B2 | 11/2007 | Westbrook et al. | |
| 10,213,164 B2 * | 2/2019 | Garudadri ............ | A61B 5/0024 |
| 10,939,873 B2 * | 3/2021 | Garudadri .......... | G06K 9/00496 |
| 2002/0052539 A1 | 5/2002 | Haller et al. | |
| 2002/0165462 A1 | 11/2002 | Westbrook et al. | |
| 2003/0065269 A1 | 4/2003 | Vetter et al. | |
| 2004/0106164 A1 | 6/2004 | Brown et al. | |
| 2004/0213407 A1 | 10/2004 | Fujita et al. | |
| 2005/0027207 A1 | 2/2005 | Westbrook et al. | |
| 2005/0069031 A1 * | 3/2005 | Sunter ..................... | H04L 1/205 375/224 |
| 2005/0164160 A1 | 7/2005 | Gunter et al. | |
| 2005/0182306 A1 | 8/2005 | Sloan | |
| 2005/0198505 A1 * | 9/2005 | Smith ................. | H04N 1/32149 713/168 |
| 2005/0280454 A1 | 12/2005 | Szajnowski | |
| 2007/0081578 A1 | 4/2007 | Fudge et al. | |
| 2007/0112545 A1 | 5/2007 | Barford | |
| 2007/0159321 A1 | 7/2007 | Ogata et al. | |
| 2007/0244669 A1 * | 10/2007 | Vogel .................. | H03M 1/0836 702/85 |
| 2008/0104163 A1 | 5/2008 | Barford | |
| 2008/0141027 A1 * | 6/2008 | Kim ..................... | H04L 9/3218 726/12 |
| 2008/0143080 A1 | 6/2008 | Burr | |
| 2008/0228446 A1 | 9/2008 | Baraniuk et al. | |
| 2009/0048785 A1 | 2/2009 | Katzir et al. | |
| 2009/0062667 A1 | 3/2009 | Fayram et al. | |
| 2009/0109919 A1 | 4/2009 | Bertrand et al. | |
| 2009/0122319 A1 | 5/2009 | Ronnekleiv et al. | |
| 2009/0157325 A1 | 6/2009 | Jung et al. | |
| 2009/0190689 A1 | 7/2009 | Blu et al. | |
| 2009/0197538 A1 | 8/2009 | Borran et al. | |
| 2009/0259133 A1 | 10/2009 | Wolfberg et al. | |
| 2010/0000824 A1 | 1/2010 | Viswanath et al. | |
| 2010/0069735 A1 | 3/2010 | Berkner | |
| 2010/0081946 A1 | 4/2010 | Garudadri et al. | |
| 2010/0082302 A1 | 4/2010 | Garudadri et al. | |
| 2010/0182950 A1 | 7/2010 | Sexton et al. | |
| 2010/0220823 A1 | 9/2010 | Biyani et al. | |
| 2011/0009711 A1 | 1/2011 | Nanikashvili et al. | |
| 2011/0025870 A1 | 2/2011 | Baraniuk et al. | |
| 2019/0125271 A1 | 5/2019 | Garudadri et al. | |

FOREIGN PATENT DOCUMENTS

| | | | |
|---|---|---|---|
| EP | 1297784 A1 | | 4/2003 |
| JP | 2005518238 A | | 6/2005 |
| JP | 2006053845 | * | 2/2006 |
| JP | 2007075372 A | | 3/2007 |
| JP | 2007184754 A | | 7/2007 |
| WO | WO 03071941 A1 | | 9/2003 |
| WO | WO 2010003672 A1 | | 1/2010 |

OTHER PUBLICATIONS

Baheti P. K., et al., "An Ultra Low Power Pulse Oximeter Sensor Based on Compressed Sensing" Wearable and Implantable Body Sensor Networks, 2009. BSN 2009. Sixth International Workshop On, IEEE, Piscataway, NJ, USA, Jun. 3, 2009 (Jun. 3, 2009), pp. 144-148, XP031522335.

Candes E. J., et al., "An Introduction to Compressive Sampling [A sensing/sampling paradigm that goes against the common knowledge in data acquisition]" IEEE Signal Processing Magazine, IEEE Service Center, Piscataway, NJ, US, vol. 24, No. 2, Mar. 1, 2008 (Mar. 1, 2008), pp. 21-30, XP011206127.

European Search Report—EP20154880—Search Authority—Munich—dated May 20, 2020.

Figueiredo M.A.T., et al., "Gradient Projection for Sparse Reconstruction: Application to Compressed Sensing and Other Inverse Problems," IEEE Journal of Selected Topics in Signal Processing, Dec. 1, 2007 (Dec. 1, 2007), pp. 586-597, vol. 1(4), XP011199163.

International Preliminary Report on Patentability—PCT/US2009/058383, The International Bureau of WIPO—Geneva, Switzerland, dated Jan. 17, 2011.

International Search Report and Written Opinion—PCT/US2009/058383—International Search Authority—European Patent Office—dated May 20, 2010.

Laska J., et al., "Random Sampling for Analog-to-information Conversion of Wideband Signals" Design, Applications, Integration and Software, 2006 IEEE Dallas/CAS Workshop On, IEEE, PI, Oct. 1, 2006 (Oct. 1, 2006), pp. 119-122, XP031052636, ISBN: 978-1-4244-0669-2, abstract , p. 3, col. 1, paragraph 1 , p. 3, col. 2, paragraph 2, p. 4, col. 1, figure 1.

Malioutov, D.M., et al., "Compressed Sensing With Sequential Observations", 2008 IEEE International Conference on Acoutics, Speech and Signal Processing, Mar. 31, 2008, pp. 3357-3360.

Pfetsch S., et al., "On the feasibility of hardware implementation of sub-Nyquist random-sampling based analog-to-information conversion" Circuits and Systems, 2008. ISCAS 2008. IEEE International Symposium On, IEEE, Piscataway, NJ, USA, May 18, 2008 (May 18, 2008), pp. 1480-1483, XP031392264.

Taiwan Search Report—TW098132585—TIPO—dated Oct. 26, 2012.

* cited by examiner (a)

(b)

|         | Nyquist-PPG      |                  |            | CS-PPG (USR=40)  |                  |            |
|---------|------------------|------------------|------------|------------------|------------------|------------|
| Patient | SBP (mmHg)       | DBP (mmHg)       | $N_{BP}$   | SBP (mmHg)       | DBP (mmHg)       | $N_{BP}$   |
| 55      | 4.72             | 3.1              | 48.8       | 2.95             | 2.19             | 13.05      |
| 212     | 4.02             | 3.12             | 75.6       | 3.97             | 1.93             | 13         |
| 213     | 4.54             | 2.27             | 21.44      | 5.54             | 2.18             | 3.3        |
| 219     | 7.68             | 3.65             | 29.8       | 8.85             | 3.14             | 6.88       |
| 221     | 8.24             | 3.85             | 81.5       | 6.67             | 4.03             | 10.4       |
| 224     | 6.47             | 4.87             | 63.05      | 6.1              | 3.84             | 12.35      |
| 230     | 6.42             | 3.3              | 37.8       | 6.09             | 3.68             | 1.52       |
| 237     | 9.25             | 6.83             | 18.61      | 7.89             | 3.62             | 5.52       |
| 408     | 8.99             | 9.06             | 73.41      | 8.46             | 6.66             | 12.4       |
| 443     | 11.42            | 7.75             | 86.93      | 7.45             | 3.97             | 5.73       |
| 444     | 7.85             | 4.08             | 59.23      | 7.49             | 4.02             | 13.1       |
| 476     | 8.92             | 5.5              | 49.96      | 7.06             | 2.49             | 15.02      |
| 482     | 7.34             | 2.97             | 16.92      | 6.1              | 2.35             | 2.83       |
| Avg:    | 7.37             | 4.64             | 51         | 6.51             | 3.39             | 8.85       |

FIG. 15

WEARABLE SYSTEM FOR CAPTURING AND TRANSMITTING BIOMEDICAL SIGNALS

CLAIM OF PRIORITY UNDER 35 U.S.C. § 119

This application is a continuation of U.S. Non-Provisional application Ser. No. 16/227,955, filed Dec. 20, 2018, now U.S. Pat. No. 10,939,873, titled "WEARABLE SYSTEM FOR CAPTURING AND TRANSMITTING BIOMEDICAL SIGNALS," which is a continuation of U.S. Non-Provisional application Ser. No. 12/512,480, filed Jul. 30, 2009, now bearing U.S. Pat. No. 10,213,164, titled "METHOD AND APPARATUS FOR UNDER-SAMPLED ACQUISITION AND TRANSMISSION OF PHOTOPLETHYSMOGRAPH (PPG) DATA AND RECONSTRUCTION OF FULL BAND PPG DATA AT THE RECEIVER," which claims the benefit and priority of U.S. Provisional Application No. 61/100,654, filed Sep. 26, 2008, titled "UNDER-SAMPLED ACQUISITION OF PPG, TRANSMISSION AND RECONSTRUCTION" and U.S. Provisional Application No. 61/101,056, filed Sep. 29, 2008, titled "UNDER-SAMPLED ACQUISITION OF PPG, TRANSMISSION AND RECONSTRUCTION," each of which are assigned to the assignee hereof and hereby expressly incorporated by reference herein.

BACKGROUND

Field

Certain aspects of the present disclosure generally relate to signal processing and, more particularly, to a method for under-sampled acquisition, transmission, and reconstruction of a signal.

Background

Compressed sensing (CS) is an emerging signal processing concept, wherein significantly fewer sensor measurements than that suggested by Shannon/Nyquist sampling theorem can be used to recover signals with arbitrarily fine resolution. This is possible when the signals being sensed are inherently compressible or sparse in certain domain. A class of band-limited signals with M non-zero spectral components is considered, where $M<<f_s/2$ and $f_s$ is a suggested sampling rate, such as the Nyquist sampling rate. Traditionally, such signals can be compressed after acquisition for more efficient transmission and/or storage.

In the CS framework, the acquisition process (i.e., sensing) can be integral to source compression and can be independent of the sparse nature of the signals. However, this sparsity information can be required at a receiver side in order to perform signal reconstruction. Measurements in the CS framework are generally defined as inner products of the signal with random basis functions. These signals can be accurately recovered if at least 2·M samples are available at the receiver, albeit with some additional computational complexity at the receiver. This can be useful in the context of a body area network (BAN) as the computational complexity is shifted to nodes with flexible power budget in order to increase working life of sensors employed in the BAN.

The CS paradigm can be used for applications concerning signal detection/classification, imaging, data compression and Magnetic Resonance Imaging (MRI). Benefits of the CS are reported in terms of improved signal fidelity and superior recognition performance. In the present disclosure, the CS-based signal processing is proposed for providing low power sensors within the BAN for healthcare and fitness applications.

Important aspect of the BAN in healthcare applications is to provide a reliable communication link between sensors (i.e., transmitters) and an aggregator (i.e., a receiver), while minimizing sensor power and communication latency. It is previously reported that up to 50% packet loss rates are observed involving a multi-hop wireless network. However, the packet loss performance can be improved by employing Quality of Service (QoS) aware networks. A dual-channel approach can be applied where one channel may be reserved for emergency alert messages. As the result, lower packet loss rates of 5% to 25% can be observed. However, the packet loss rate can increase with network congestion.

Furthermore, the use of Forward Error Correction (FAC) coding within the BAN scenarios is explored. By using FEC schemes, it can be observed a small residual packet loss rate for communication latency on the order of seconds. Also, transmission of an electro-cardiogram (ECG) signal over the General Packet Radio Service (GPRS) link is investigated, and a small loss rate is achieved for communication latency on the order of seconds. The benefits of using FEC come at the cost of increased transmission bandwidth and sensor complexity. On the other hand, a technique based on retransmissions has smaller bandwidth penalty compared to the FEC approach, but sensor complexity is considerable as packets need to be buffered at a transmitter. There is also a latency penalty proportional to a round trip time.

Therefore, there is a need in the art for methods with lower bandwidth overhead and lower computational complexity at the transmitter leading to a longer sensor life, while not compromising application specific objective quality metrics for a given packet loss rate.

SUMMARY

Certain aspects provide a method for signal processing. The method generally includes generating, at an apparatus, non-uniform sampling instances, and sensing samples of a signal during a plurality of the non-uniform sampling instances.

Certain aspects provide an apparatus for signal processing. The apparatus generally includes a generator configured to generate non-uniform sampling instances, and a sensor configured to sense samples of a signal during a plurality of the non-uniform sampling instances.

Certain aspects provide an apparatus for signal processing. The apparatus generally includes means for generating non-uniform sampling instances, and means for sensing samples of a signal during a plurality of the non-uniform sampling instances.

Certain aspects provide a computer-program product for signal processing. The computer-program product includes a computer-readable medium comprising instructions executable to generate non-uniform sampling instances, and sense samples of a signal during a plurality of the non-uniform sampling instances.

Certain aspects provide a sensing device. The sensing device generally includes a generator configured to generate non-uniform sampling instances, a sensor configured to sense samples of a signal at least during a plurality of the non-uniform sampling instances, and a transmitter configured to transmit the sensed samples.

Certain aspects provide a method for signal processing. The method generally includes receiving, at an apparatus, samples of a signal from another apparatus, determining a set of non-uniform sampling instances during which the signal was sampled at the other apparatus, and reconstructing the signal from the received samples using the determined set of non-uniform sampling instances.

Certain aspects provide an apparatus for signal processing. The apparatus generally includes a receiver configured to receive samples of a signal transmitted from another apparatus, a circuit configured to determine a set of non-uniform sampling instances during which the signal was sampled at the other apparatus, and a re-constructor configured to reconstruct the signal from the received samples using the determined set of non-uniform sampling instances.

Certain aspects provide an apparatus for signal processing. The apparatus generally includes means for receiving samples of a signal transmitted from another apparatus, means for determining a set of non-uniform sampling instances during which the signal was sampled at the other apparatus, and means for reconstructing the signal from the received samples using the determined set of non-uniform sampling instances.

Certain aspects provide a computer-program product for signal processing. The computer-program product includes a computer-readable medium comprising instructions executable to receive samples of a signal transmitted from an apparatus, determine a set of non-uniform sampling instances during which the signal was sampled at the apparatus, and reconstruct the signal from the received samples using the determined set of non-uniform sampling instances.

Certain aspects provide a headset. The headset generally includes a receiver configured to receive samples of a signal transmitted from an apparatus, a circuit configured to determine a set of non-uniform sampling instances during which the signal was sampled at the apparatus, a re-constructor configured to reconstruct the signal from the received samples using the determined set of non-uniform sampling instances; and a transducer configured to provide an audio output based on the reconstructed signal.

Certain aspects provide a watch. The watch generally includes a receiver configured to receive samples of a signal transmitted from an apparatus, a circuit configured to determine a set of non-uniform sampling instances during which the signal was sampled at the apparatus, a re-constructor configured to reconstruct the signal from the received samples using the determined set of non-uniform sampling instances; and a user interface configured to provide an indication based on the reconstructed signal.

Certain aspects provide a monitoring device. The monitoring device generally includes a connector, a receiver configured to receive via the connector samples of a signal transmitted from an apparatus, a circuit configured to determine a set of non-uniform sampling instances during which the signal was sampled at the apparatus, a re-constructor configured to reconstruct the signal from the received samples using the determined set of non-uniform sampling instances, and a user interface configured to provide an indication based on the reconstructed signal.

Certain aspects provide a method for signal processing. The method generally includes actuating a source during a plurality of non-uniform sampling instances, and de-actuating the source between the plurality of the non-uniform sampling instances.

Certain aspects provide an apparatus for signal processing. The apparatus generally includes an actuating circuit configured to actuate a source during a plurality of non-uniform sampling instances, and a de-actuating circuit configured to de-actuate the source between the plurality of the non-uniform sampling instances.

Certain aspects provide an apparatus for signal processing. The apparatus generally includes means for actuating a source during a plurality of non-uniform sampling instances, and means for de-actuating the source between the plurality of the non-uniform sampling instances.

Certain aspects provide a computer-program product for signal processing. The computer-program product includes a computer-readable medium comprising instructions executable to actuate a source during a plurality of non-uniform sampling instances, and de-actuate the source between the plurality of the non-uniform sampling instances.

Certain aspects provide a sensing device. The sensing device generally includes an actuating circuit configured to actuate a source during a plurality of non-uniform sampling instances, a sensor configured to sense samples of a signal during the plurality of the non-uniform sampling instances, and a de-actuating circuit configured to de-actuate the source between the plurality of the non-uniform sampling instances.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

FIG. 15 illustrates standard deviations for a systolic blood pressure (SBP) estimation error and a diastolic blood pressure (DBP) estimation error in accordance with certain aspects of the present disclosure.

DETAILED DESCRIPTION

Figure 1:
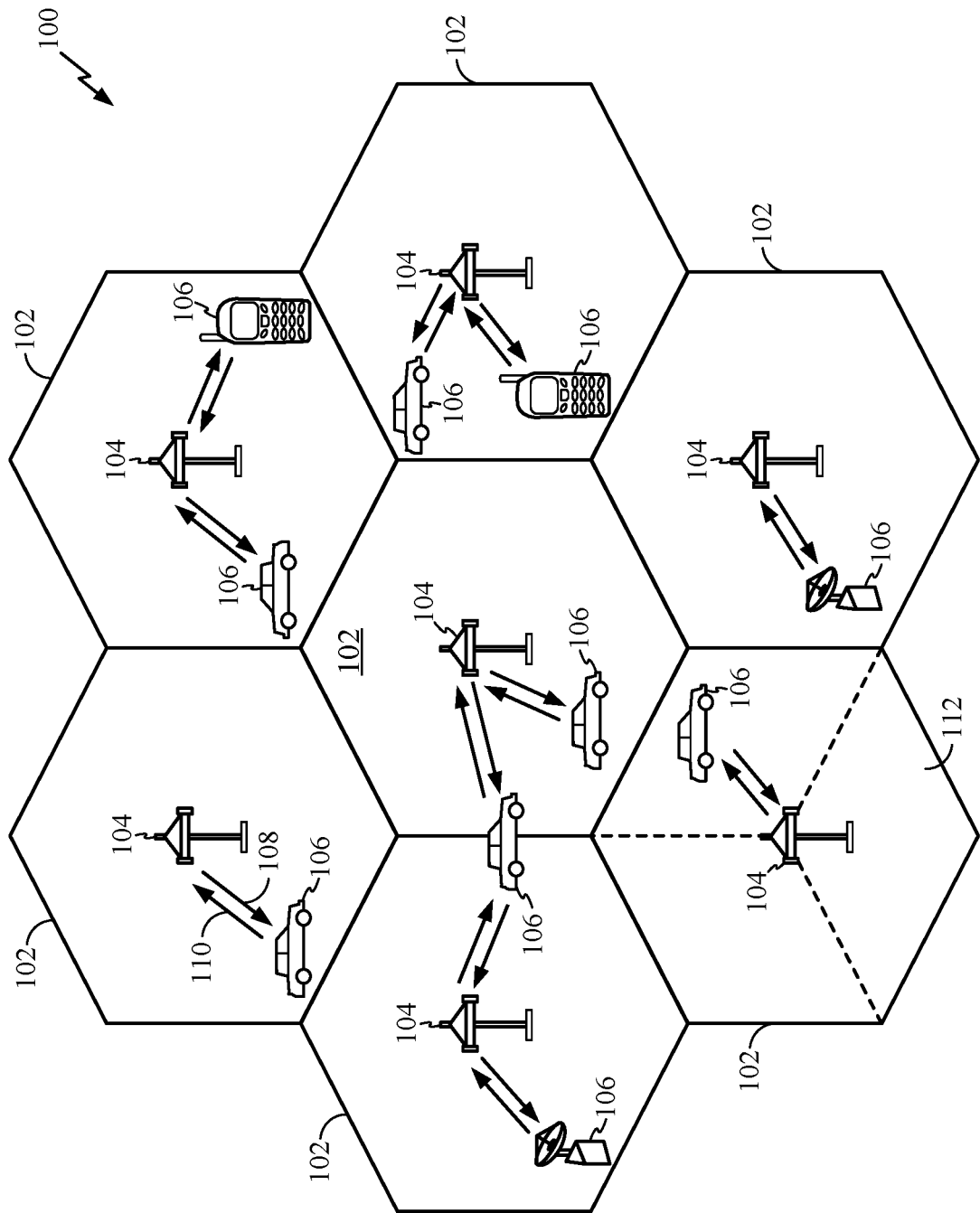
FIG. 1 illustrates an example wireless communication system, in accordance with certain aspects of the present disclosure.

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

The word "exemplary" is used herein to mean "serving as an example, instance, or illustration." Any aspect described herein as "exemplary" is not necessarily to be construed as preferred or advantageous over other aspects.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different wireless technologies, system configurations, networks, and transmission protocols, some of which are illustrated by way of example in the figures and in the following description of the preferred aspects. The detailed description and drawings are merely illustrative of the disclosure rather than limiting, the scope of the disclosure being defined by the appended claims and equivalents thereof.

An Example Wireless Communication System

The techniques described herein may be used for various broadband wireless communication systems, including communication systems that are based on an orthogonal multiplexing scheme and a single carrier transmission. Examples of such communication systems include Orthogonal Frequency Division Multiple Access (OFDMA) systems, Single-Carrier Frequency Division Multiple Access (SC-FDMA) systems, Code Division Multiple Access (CDMA), and so forth. An OFDMA system utilizes orthogonal frequency division multiplexing (OFDM), which is a modulation technique that partitions the overall system bandwidth into multiple orthogonal sub-carriers. These sub-carriers may also be called tones, bins, etc. With OFDM, each subcarrier may be independently modulated with data. An SC-FDMA system may utilize interleaved FDMA (IFDMA) to transmit on sub-carriers that are distributed across the system bandwidth, localized FDMA (LFDMA) to transmit on a block of adjacent sub-carriers, or enhanced FDMA (EFDMA) to transmit on multiple blocks of adjacent sub-carriers. In general, modulation symbols are sent in the frequency domain with OFDM and in the time domain with SC-FDMA. A CDMA system may utilize spread-spectrum technology and a coding scheme where each transmitter (i.e., user) is assigned a code in order to allow multiple users to be multiplexed over the same physical channel.

One specific example of a communication system based on an orthogonal multiplexing scheme is a WiMAX system. WiMAX, which stands for the Worldwide Interoperability for Microwave Access, is a standards-based broadband wireless technology that provides high-throughput broadband connections over long distances. There are two main applications of WiMAX today: fixed WiMAX and mobile WiMAX. Fixed WiMAX applications are point-to-multipoint, enabling broadband access to homes and businesses, for example. Mobile WiMAX offers the full mobility of cellular networks at broadband speeds.

IEEE 802.16x is an emerging standard organization to define an air interface for fixed and mobile broadband wireless access (BWA) systems. IEEE 802.16x approved "IEEE P802.16d/D5-2004" in May 2004 for fixed BWA systems and published "IEEE P802.16e/D12 Oct. 2005" in October 2005 for mobile BWA systems. The latest revision of the IEEE 802.16, "IEEE P802.16Rev2/D8 Dec. 2008", a draft standard, now consolidates materials from IEEE 802.16e and corrigendum. The standards define four different physical layers (PHYs) and one medium access control (MAC) layer. The OFDM and OFDMA physical layer of the four physical layers are the most popular in the fixed and mobile BWA areas respectively.

The teachings herein may be incorporated into (e.g., implemented within or performed by) a variety of wired or wireless apparatuses (e.g., nodes). In some aspects, a node implemented in accordance with the teachings herein may comprise an access point or an access terminal.

An access point ("AP") may comprise, be implemented as, or known as NodeB, Radio Network Controller ("RNC"), eNodeB, Base Station Controller ("BSC"), Base Transceiver Station ("BTS"), Base Station ("BS"), Transceiver Function ("TF"), Radio Router, Radio Transceiver, Basic Service Set ("BSS"), Extended Service Set ("ESS"), Radio Base Station ("RBS"), or some other terminology.

An access terminal ("AT") may comprise, be implemented as, or known as an access terminal, a subscriber station, a subscriber unit, a mobile station, a remote station, a remote terminal, a user terminal, a user agent, a user device, user equipment, or some other terminology. In some implementations an access terminal may comprise a cellular telephone, a cordless telephone, a Session Initiation Protocol ("SIP") phone, a wireless local loop ("WLL") station, a personal digital assistant ("PDA"), a handheld device having wireless connection capability, or some other suitable processing device connected to a wireless modem. Accordingly, one or more aspects taught herein may be incorporated into a phone (e.g., a cellular phone or smart phone), a computer (e.g., a laptop), a portable communication device, a portable computing device (e.g., a personal data assistant), an entertainment device (e.g., a music or video device, or a satellite radio), a global positioning system device, or any other suitable device that is configured to communicate via a wireless or wired medium. In some aspects the node is a wireless node. Such wireless node may provide, for example, connectivity for or to a network (e.g., a wide area network such as the Internet or a cellular network) via a wired or wireless communication link.

FIG. 1 illustrates an example of a wireless communication system 100 in which aspects of the present disclosure may be employed. The wireless communication system 100 may be a broadband wireless communication system. The wireless communication system 100 may provide communication for a number of cells 102, each of which is serviced by a base station 104. A base station 104 may be a fixed station that communicates with user terminals 106. The base station 104 may alternatively be referred to as an access point, a Node B or some other terminology.

FIG. 1 depicts various user terminals 106 dispersed throughout the system 100. The user terminals 106 may be fixed (i.e., stationary) or mobile. The user terminals 106 may alternatively be referred to as remote stations, access terminals, terminals, subscriber units, mobile stations, stations, user equipment, etc. The user terminals 106 may be wireless devices, such as cellular phones, personal digital assistants (PDAs), handheld devices, wireless modems, laptop computers, personal computers, etc.

A variety of algorithms and methods may be used for transmissions in the wireless communication system 100 between the base stations 104 and the user terminals 106. For example, signals may be sent and received between the base stations 104 and the user terminals 106 in accordance with OFDM/OFDMA techniques. If this is the case, the wireless communication system 100 may be referred to as an OFDM/OFDMA system. Alternatively, signals may be sent and received between the base stations 104 and the user terminals 106 in accordance with CDMA technique. If this is the case, the wireless communication system 100 may be referred to as a CDMA system.

A communication link that facilitates transmission from a base station 104 to a user terminal 106 may be referred to as a downlink (DL) 108, and a communication link that facilitates transmission from a user terminal 106 to a base station 104 may be referred to as an uplink (UL) 110. Alternatively, a downlink 108 may be referred to as a forward link or a forward channel, and an uplink 110 may be referred to as a reverse link or a reverse channel.

A cell 102 may be divided into multiple sectors 112. A sector 112 is a physical coverage area within a cell 102. Base stations 104 within a wireless communication system 100 may utilize antennas that concentrate the flow of power within a particular sector 112 of the cell 102. Such antennas may be referred to as directional antennas.

Figure 2:
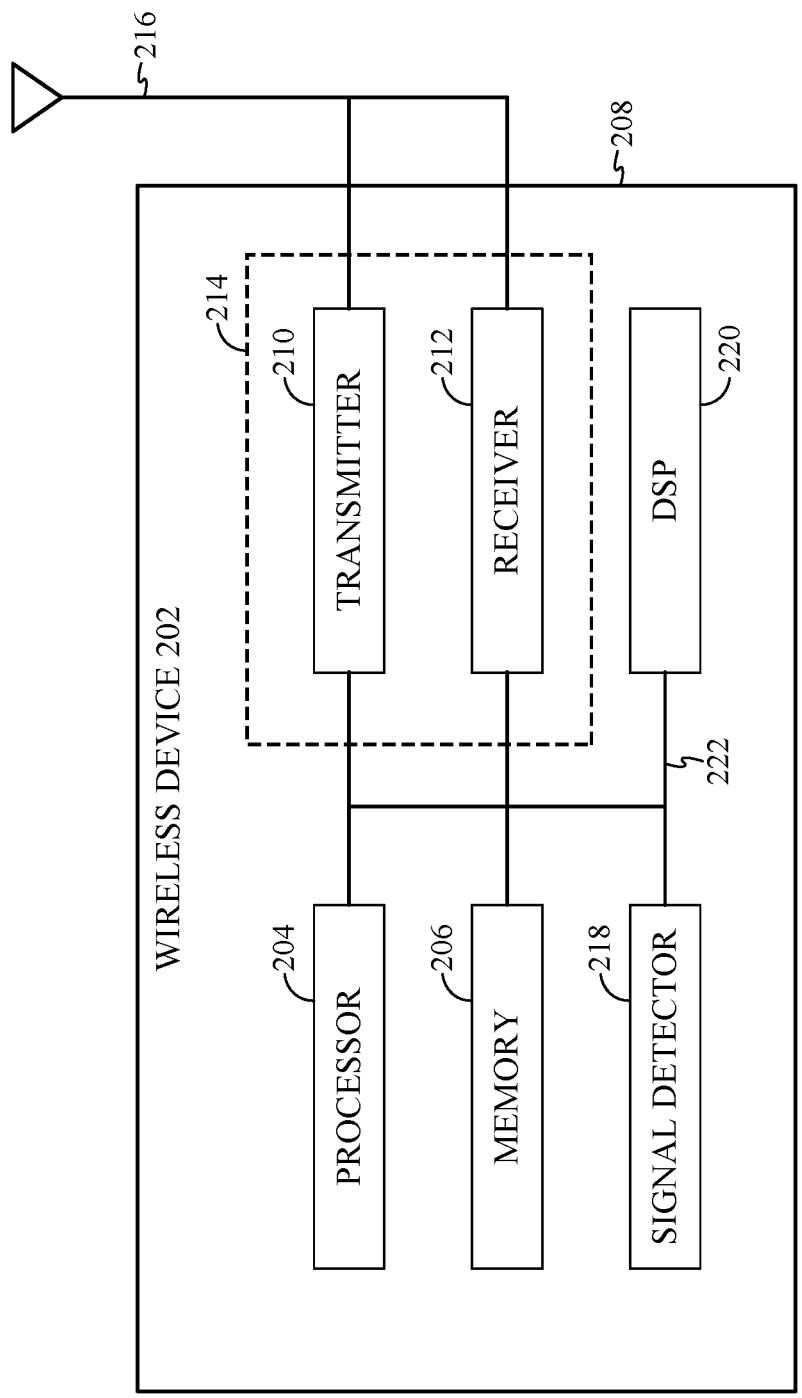
FIG. 2 illustrates various components that may be utilized in a wireless device in accordance with certain aspects of the present disclosure.

FIG. 2 illustrates various components that may be utilized in a wireless device 202 that may be employed within the wireless communication system 100. The wireless device 202 is an example of a device that may be configured to implement the various methods described herein. The wireless device 202 may be a base station 104 or a user terminal 106.

The wireless device 202 may include a processor 204 which controls operation of the wireless device 202. The processor 204 may also be referred to as a central processing unit (CPU). Memory 206, which may include both read-only memory (ROM) and random access memory (RAM), provides instructions and data to the processor 204. A portion of the memory 206 may also include non-volatile random access memory (NVRAM). The processor 204 typically performs logical and arithmetic operations based on program instructions stored within the memory 206. The instructions in the memory 206 may be executable to implement the methods described herein.

The wireless device 202 may also include a housing 208 that may include a transmitter 210 and a receiver 212 to allow transmission and reception of data between the wireless device 202 and a remote location. The transmitter 210 and receiver 212 may be combined into a transceiver 214. An antenna 216 may be attached to the housing 208 and electrically coupled to the transceiver 214. The wireless device 202 may also include (not shown) multiple transmitters, multiple receivers, multiple transceivers, and/or multiple antennas.

The wireless device 202 may also include a signal detector 218 that may be used in an effort to detect and quantify the level of signals received by the transceiver 214. The signal detector 218 may detect such signals as total energy, energy per subcarrier per symbol, power spectral density and other signals. The wireless device 202 may also include a digital signal processor (DSP) 220 for use in processing signals.

The various components of the wireless device 202 may be coupled together by a bus system 222, which may include a power bus, a control signal bus, and a status signal bus in addition to a data bus.

Figure 3:
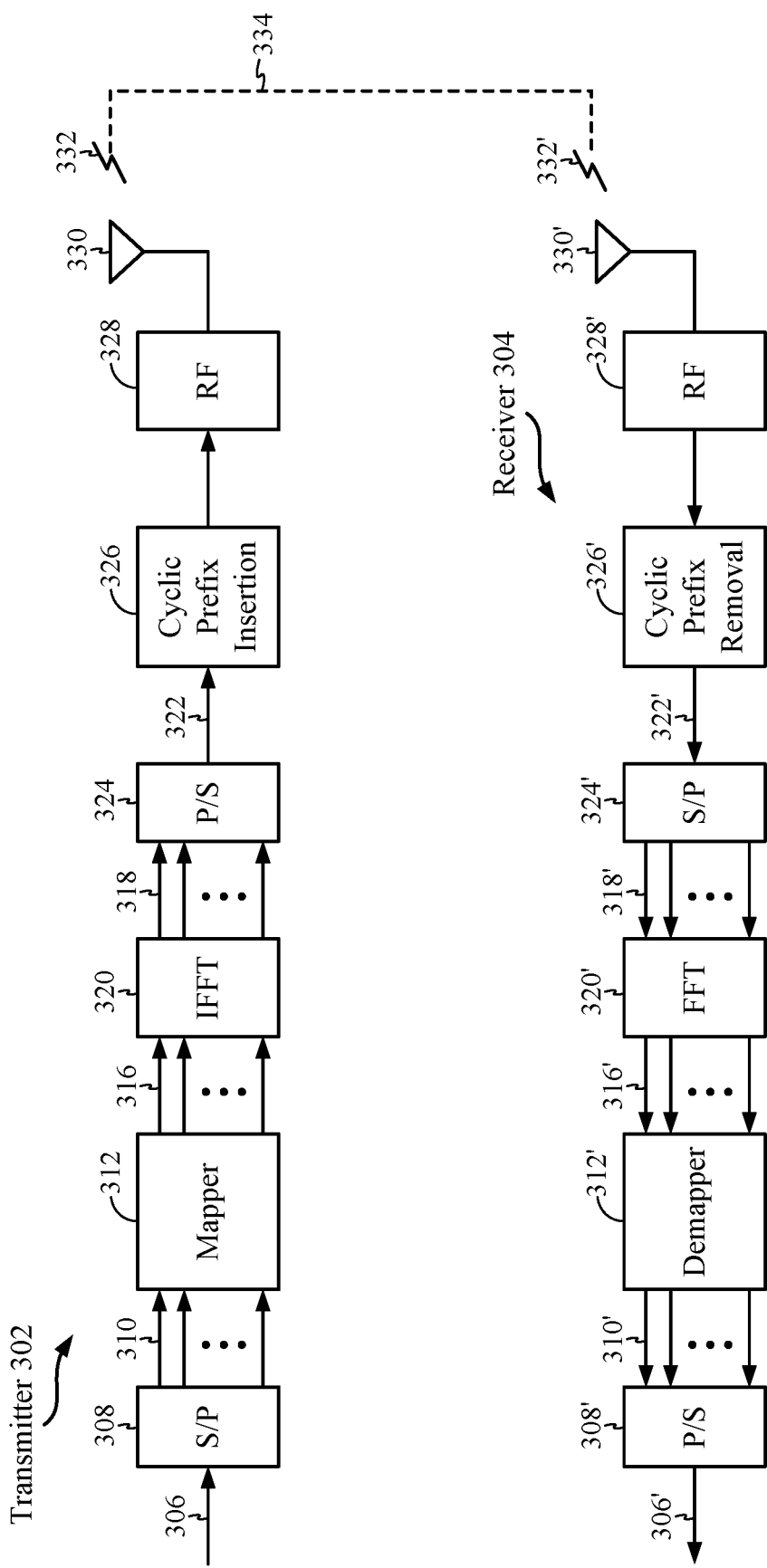
FIG. 3 illustrates an example transmitter and an example receiver that may be used within a wireless communication system in accordance with certain aspects of the present disclosure.

FIG. 3 illustrates an example of a transmitter 302 that may be used within a wireless communication system 100 that utilizes OFDM/OFDMA. Portions of the transmitter 302 may be implemented in the transmitter 210 of a wireless device 202. The transmitter 302 may be implemented in a base station 104 for transmitting data 306 to a user terminal 106 on a downlink 108. The transmitter 302 may also be implemented in a user terminal 106 for transmitting data 306 to a base station 104 on an uplink 110.

Data 306 to be transmitted is shown being provided as input to a serial-to-parallel (S/P) converter 308. The S/P converter 308 may split the transmission data into M parallel data streams 310.

The N parallel data streams 310 may then be provided as input to a mapper 312. The mapper 312 may map the N parallel data streams 310 onto N constellation points. The mapping may be done using some modulation constellation, such as binary phase-shift keying (BPSK), quadrature phase-shift keying (QPSK), 8 phase-shift keying (8PSK), quadrature amplitude modulation (QAM), etc. Thus, the mapper 312 may output N parallel symbol streams 316, each symbol stream 316 corresponding to one of the N orthogonal subcarriers of the inverse fast Fourier transform (IFFT) 320. These N parallel symbol streams 316 are represented in the frequency domain and may be converted into N parallel time domain sample streams 318 by an IFFT component 320.

A brief note about terminology will now be provided. N parallel modulations in the frequency domain are equal to N modulation symbols in the frequency domain, which are equal to N mapping and N-point IFFT in the frequency domain, which is equal to one (useful) OFDM symbol in the time domain, which is equal to N samples in the time domain. One OFDM symbol in the time domain, Ns, is equal to $N_{CP}$ (the number of cyclic prefix (CP) samples per OFDM symbol)+N (the number of useful samples per OFDM symbol).

The N parallel time domain sample streams 318 may be converted into an OFDM/OFDMA symbol stream 322 by a parallel-to-serial (P/S) converter 324. A cyclic prefix insertion component 326 may insert a CP between successive OFDM/OFDMA symbols in the OFDM/OFDMA symbol stream 322. The output of the CP insertion component 326 may then be upconverted to a desired transmit frequency band by a radio frequency (RF) front end 328. An antenna 330 may then transmit the resulting signal 332.

FIG. 3 also illustrates an example of a receiver 304 that may be used within a wireless device 202 that utilizes OFDM/OFDMA. Portions of the receiver 304 may be implemented in the receiver 212 of a wireless device 202. The receiver 304 may be implemented in a user terminal 106 for receiving data 306 from a base station 104 on a downlink 108. The receiver 304 may also be implemented in a base station 104 for receiving data 306 from a user terminal 106 on an uplink 110.

The transmitted signal 332 is shown traveling over a wireless channel 334. When a signal 332' is received by an antenna 330', the received signal 332' may be downconverted to a baseband signal by an RF front end 328'. A CP removal component 326' may then remove the CP that was inserted between OFDM/OFDMA symbols by the CP insertion component 326.

The output of the CP removal component 326' may be provided to an S/P converter 324'. The S/P converter 324' may divide the OFDM/OFDMA symbol stream 322' into the N parallel time-domain symbol streams 318', each of which corresponds to one of the N orthogonal subcarriers. A fast Fourier transform (FFT) component 320' may convert the N parallel time-domain symbol streams 318' into the frequency domain and output N parallel frequency-domain symbol streams 316'.

A demapper 312' may perform the inverse of the symbol mapping operation that was performed by the mapper 312 thereby outputting N parallel data streams 310'. A P/S converter 308' may combine the N parallel data streams 310' into a single data stream 306'. Ideally, this data stream 306' corresponds to the data 306 that was provided as input to the transmitter 302. Note that elements 308', 310', 312', 316', 320', 318' and 324' may all be found in a baseband processor 340'.

Body Area Network Concept

Figure 4:
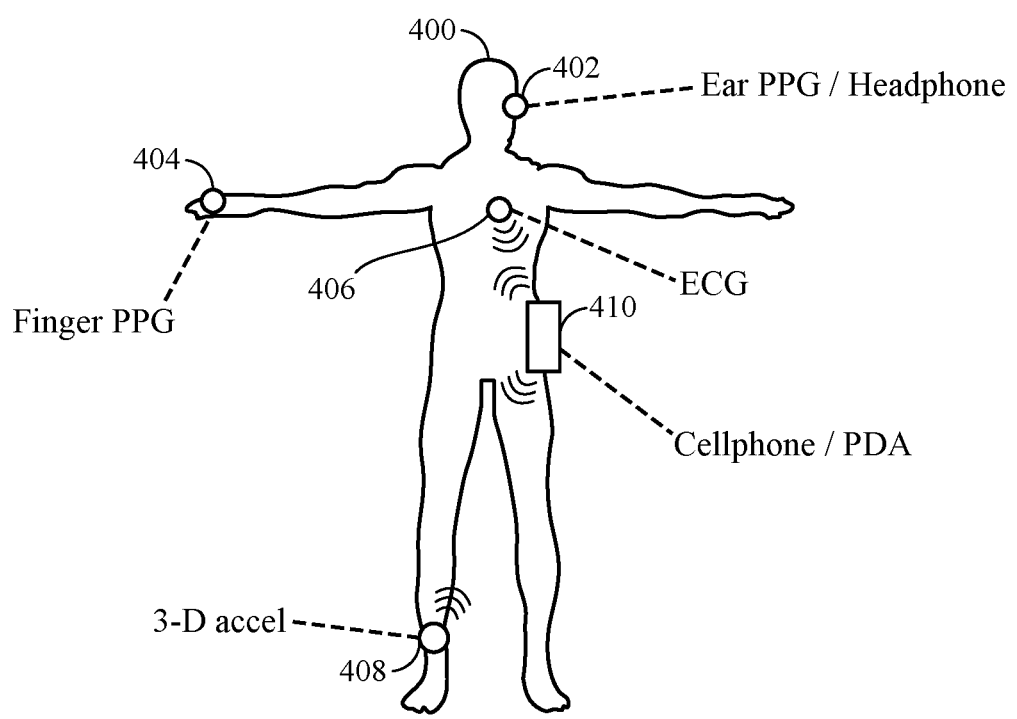
FIG. 4 illustrates an example of a body area network (BAN) in accordance with certain aspects of the present disclosure.

FIG. 4 illustrates an example of a body area network (BAN) 400 that may correspond to the wireless system 100 illustrated in FIG. 1. Body area networks represent a promising concept for healthcare applications such as continuous monitoring for diagnostic purposes, effects of medicines on chronic ailments, etc.

Figure 5:
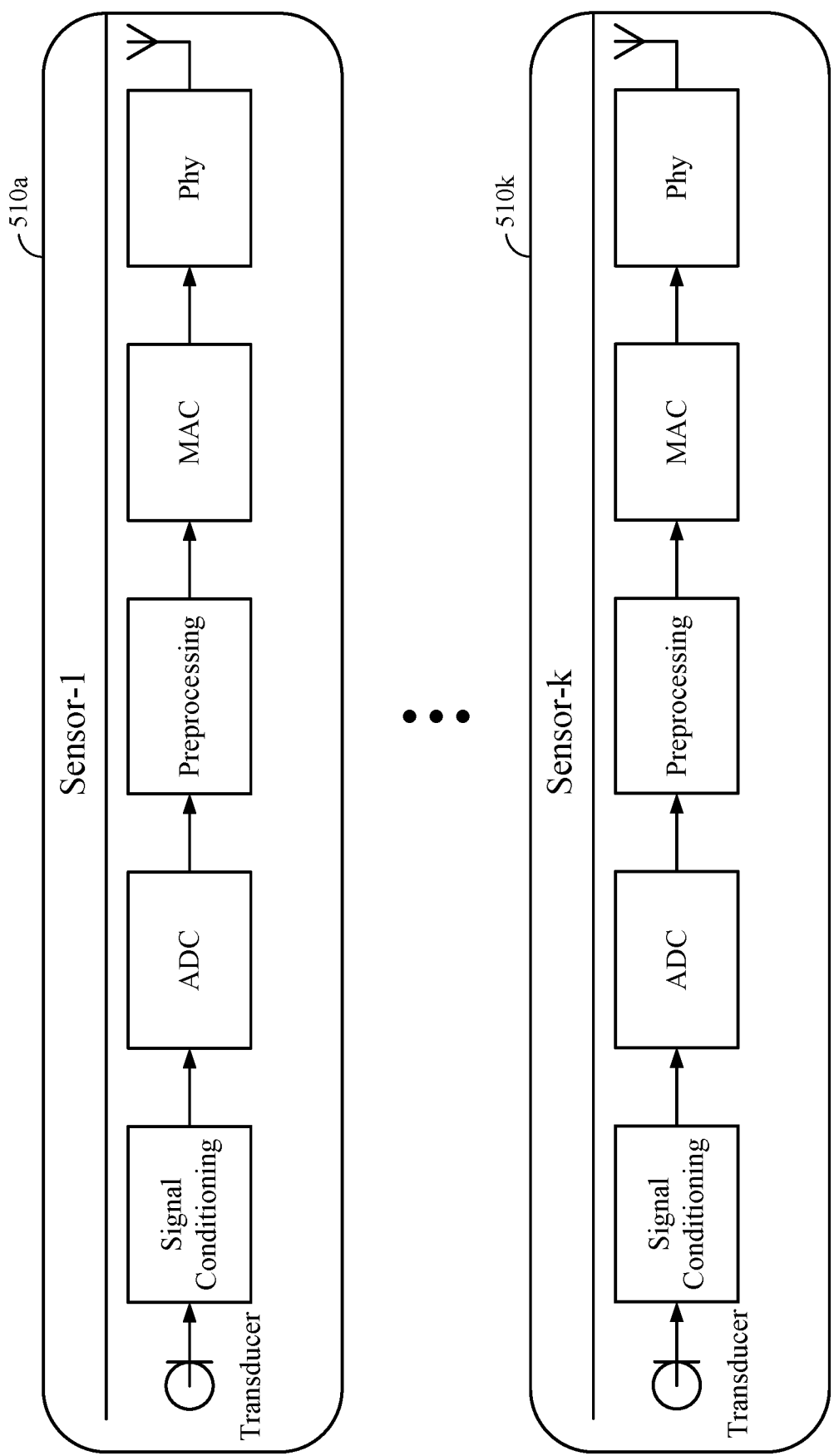
FIG. 5 illustrates an example block diagram of array of sensors used within the BAN in accordance with certain aspects of the present disclosure.

The BAN may consist of several acquisition circuits. Each acquisition circuit may comprise wireless sensor that senses one or more vital signs and communicates them to an aggregator (i.e., an access terminal) such as a mobile handset, a wireless watch, or a Personal Data Assistant (PDA). Sensors 402, 404, 406, and 408 that acquire various biomedical signals and transmit them over a wireless channel to an aggregator 410 may have the same functionality as access points 104. FIG. 5 illustrates detailed block diagram of an array of biomedical sensors 510a-510k that may correspond to sensors 402-408 within the BAN 400. Each sensor 510a-510k may be an example of the transmitter 210 from FIG. 2 and the transmitter 302 from FIG. 3.

Figure 6:
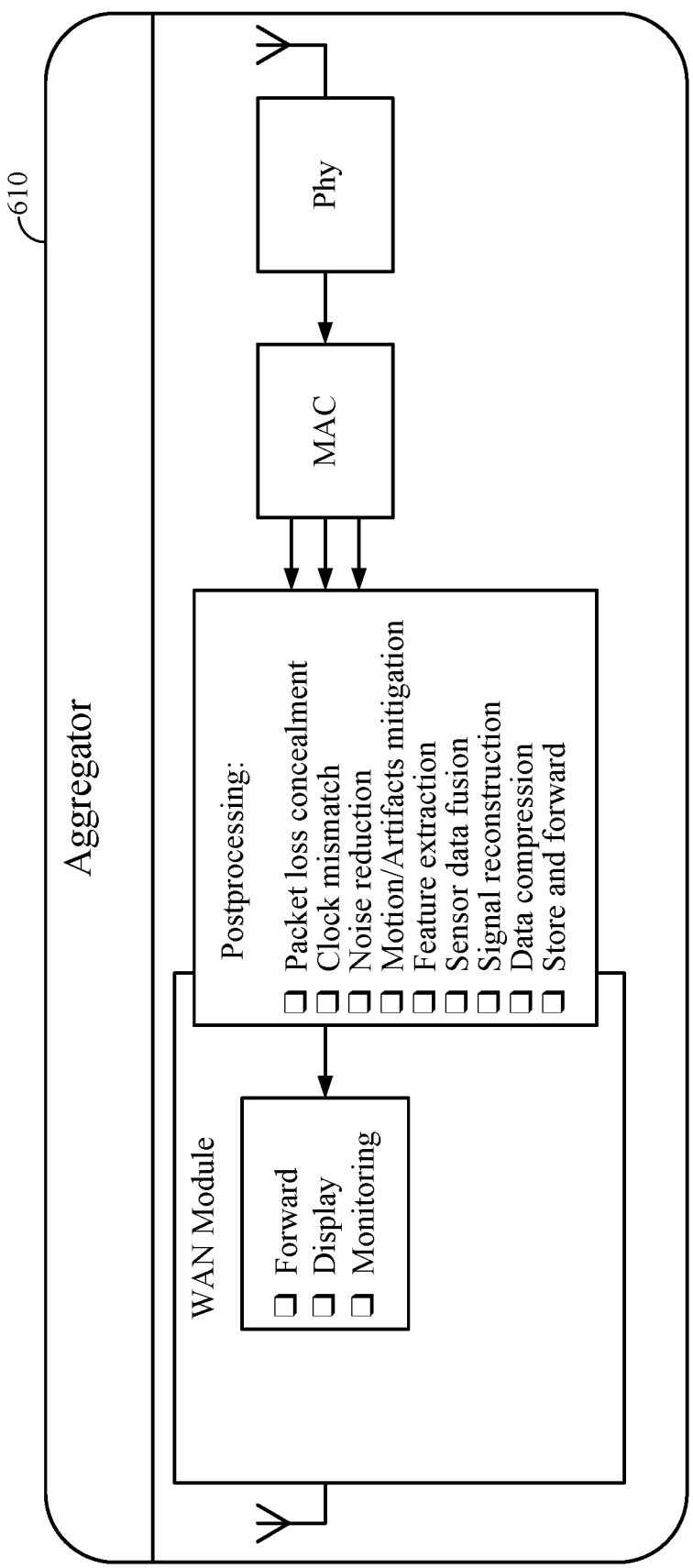
FIG. 6 illustrates an example block diagram of an aggregator used within the BAN in accordance with certain aspects of the present disclosure.

The aggregator 410 illustrated in FIG. 4 may receive and process various biomedical signals transmitted over a wireless channel from sensors 402-408. The aggregator 410 may be a mobile handset or a PDA, and may have the same functionality as a mobile device 106 from FIG. 1. FIG. 6 illustrates a detailed block diagram of an aggregator 610 that may correspond to the aggregator 410 within the BAN 400. The aggregator 610 may be an example of the receiver 212 from FIG. 2 and the receiver 304 from FIG. 3.

It is desirable for sensors used in the BAN to be non-intrusive and long lasting. Photoplethysmograph (PPG) and Electro Cardiogram (ECG) signals may be considered in this disclosure to demonstrate benefits of compressed sensing (CS) techniques for sensor signal processing. The PPG, the ECG and the activity sensing cover a large percentage of chronic ailments in a large segment of human population, and thus provide significant opportunities for wireless technologies in the BAN and mobile devices with wireless area network (WAN) connectivity.

Figure 7:
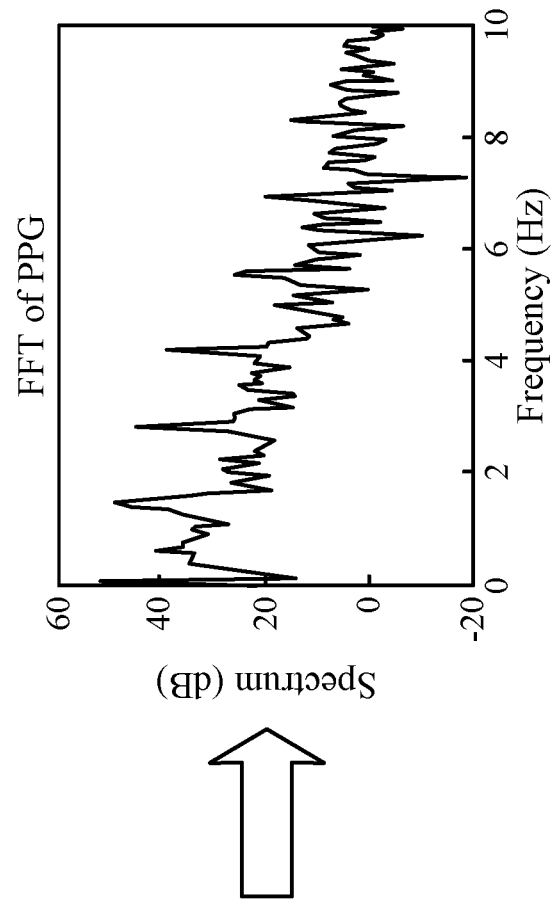
FIG. 7 illustrates an example of a time-domain photoplethysmograph (PPG) signal and its frequency spectrum in accordance with certain aspects of the present disclosure.
Figure 7:
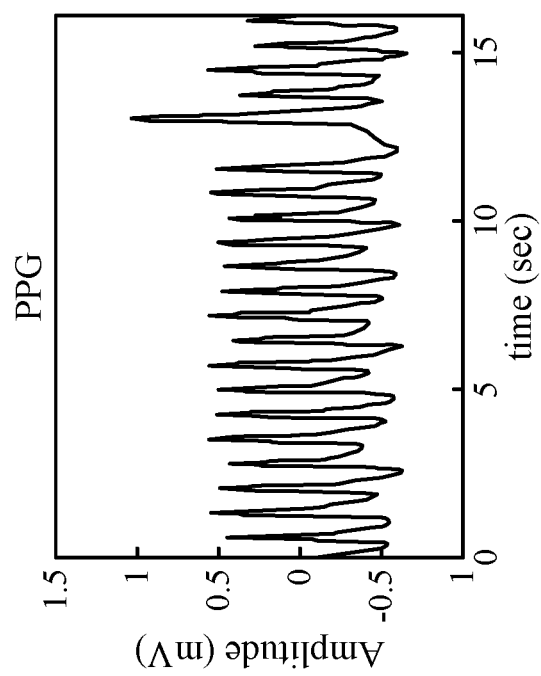

Pulse oximeter sensors can generate the PPG waveform which may enable continuous monitoring of blood oxygenation (also called $S_pO_2$), a crucial indicator of pulmonary system including lungs and respiration. A blood carries oxygen, nutrients and chemicals to the body cells in order to ensure their survival, proper functioning and to remove the cellular wastes. $S_pO_2$ is extensively used in clinical settings for diagnosis, long term monitoring, surgery, etc. FIG. 7 illustrates an example of a time-domain PPG signal and its frequency spectrum.

Figure 8:
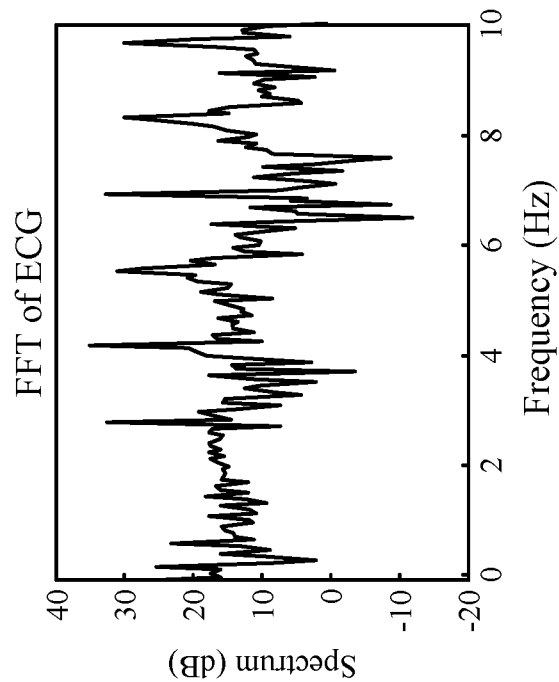
FIG. 8 illustrates an example of a time-domain electrocardiogram (ECG) signal and its frequency spectrum in accordance with certain aspects of the present disclosure.
Figure 8:
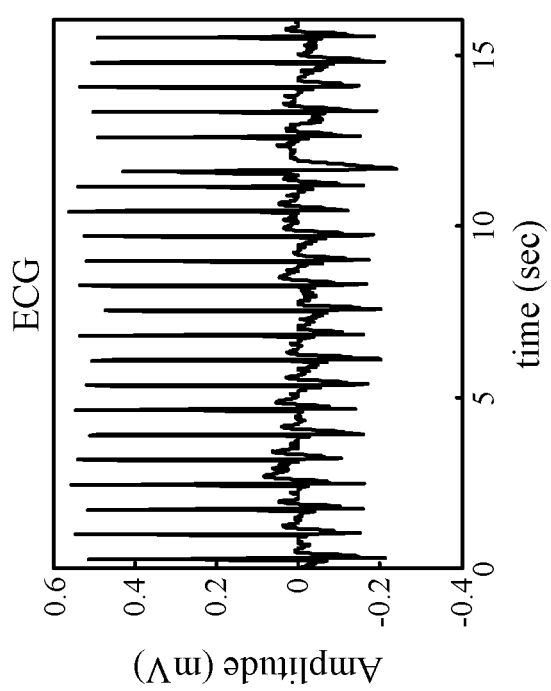

The ECG is another important vital sign for assessing the cardiovascular system. Heart is one of the most hard working body parts, pumping about six liters of blood per minute through the body in humans. Electrical signals generated during each cardiac cycle form the ECG and can be easily captured by Ag/AgCl electrode sensors. The ECG may be routinely used in clinical settings for diagnosing heart related problems and continuous monitoring of the ECG may enable early diagnosis of many chronic conditions. FIG. 8 illustrates an example of a time-domain ECG signal and its frequency spectrum.

A blood pressure (BP) is another vital sign with enormous clinical value. A systolic blood pressure (SBP) and a diastolic blood pressure (DBP) may be estimated using the ECG and the PPG signals.

Overview of Proposed Methods

Certain aspects of the present disclosure relates to methods for reducing power consumption of a pulse oximeter sensor. Commercial pulse oximeters may typically consume power in the order of 20-60 mW. The red and infrared light-emitting diodes (LEDs) account for most of this power. A power-efficient design for a PPG sensor may bring the power consumption down to 1.5 mW. The duty cycle associated with LED lighting may be reduced for a given uniform sampling rate. Fast detectors and higher clock frequencies may be used among other optimizations. Thus, the LED may be switched on for $T \cdot f_s$ duration, where $f_s$ and T represent the sampling rate and duration of lighting required to acquire each sample, respectively.

The PPG signals may be sparse in a spectral domain, and hence compressible. This may enable the usage of a compressed sensing (CS) framework in order to acquire the PPG signals. The PPG signals may be sampled at non-uniform (i.e., random) time intervals, but with an average sampling rate of $F_s$. In the CS approach, the sampling rate $F_s$ may be much smaller than the uniform sampling rate $f_s$. A factor $f_s/F_s$ may be referred as an under-sampling ratio (USR). It can be noted that this sampling approach may result in a reduced power consumption (i.e., approximately by a factor of USR) of pulse oximeter sensors used for PPG acquisition, as the LED may be lit up for only $T \cdot f_s/USR$ duration instead of $T \cdot f_s$.

Figure 9:
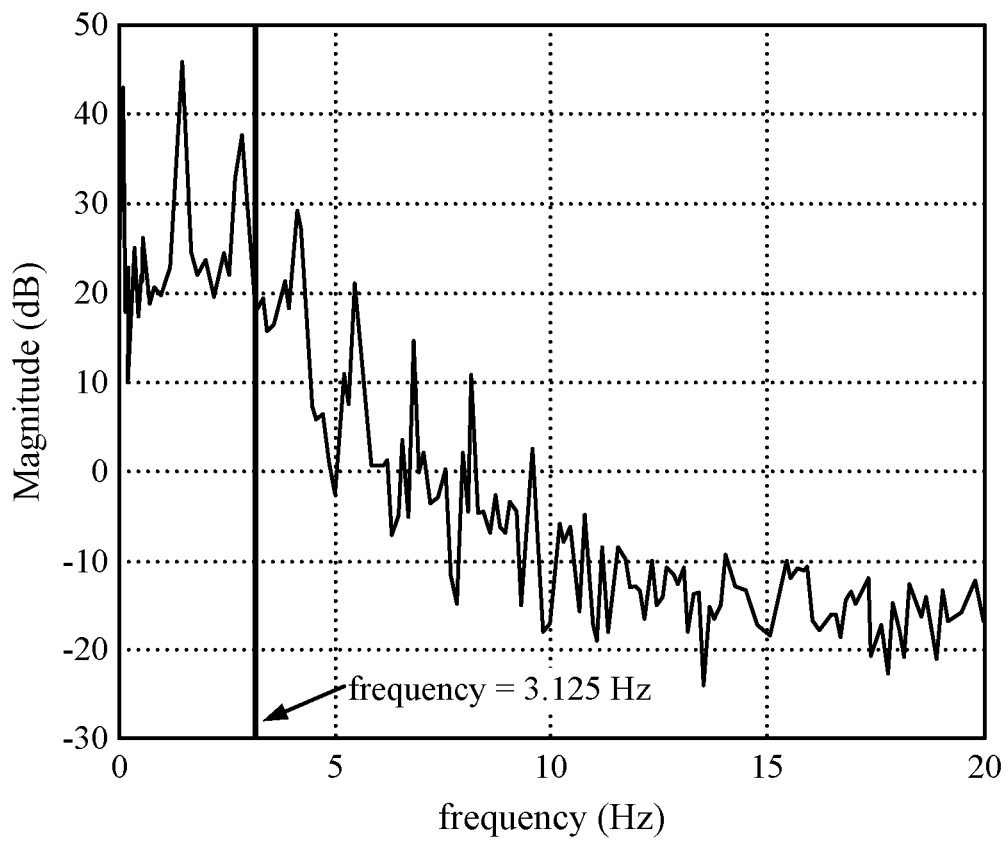
FIG. 9 illustrates another example of a frequency spectrum of a PPG signal in accordance with certain aspects of the present disclosure.

A benefit of the CS-based approach compared to low pass filtering and sampling at $f_s/USR$ is that the signal content above $f_s/USR$ may not be lost. Similarly, narrow-band signals at higher frequencies may also be acquired with a high USR. FIG. 9 illustrates an example spectrum of the PPG signal sampled at $f_s=125$ Hz. It can be observed that significant spectral content may be lost if only a low-pass filter is applied to the PPG signal and sampled at $f_s/40=3.125$ Hz for an USR of 40.

Another benefit of utilizing the CS framework is that the measurements may be independent of the transform space used at reconstruction, including the Fourier space as in traditional Nyquist rate sampling. The CS measurement framework may translate into significant power-savings on the sensor side at the cost of increased computational overhead at the receiver to reconstruct an approximation of the PPG signal.

It is also interesting to evaluate the receiver complexity for a given task, as required computations may be hosted on a mobile handset or a PDA. For example, heart rate (HR) estimation task may not require an intermediate representation of the PPG signal from the CS samples, and thus the post-processing complexity can be different for tasks such as PPG signal reconstruction and HR estimation.

A multi-parameter intelligent monitoring for intensive care (MIMIC) database can be used to demonstrate that the HR and BP estimation accuracy may not be compromised in the CS framework with different values of USR. The MIMIC database consists of simultaneous recordings of ECG, PPG and BP from several hemodynamically unstable subjects (i.e., subjects whose ECG, PPG and BP patterns may vary during a given period of observation) spanning over more than 24 hours.

Certain aspects of the present disclosure support utilizing the CS framework for packet loss mitigation during transmission of signals. This can be possible because the receiver may be equipped to reconstruct signals from a sparse representation. Wireless transport of biomedical signals from the sensing module to the aggregator is considered. For example, raw ECG data may be encoded using random projections (e.g., Rademacher patterns), and resulting random coefficients may be packetized for transmission over the air.

The sparse nature of the encoded ECG signal may allow performing a reconstruction using a subset of these random coefficients, where the subset cardinality may depend upon sparsity information. This suggests that the ECG signal may be still reconstructed and the HR estimation may be performed at the receiver despite losing some packets due to channel errors. A benefit of this approach is that retransmissions may not be required, resulting in a lower latency and a simpler protocol stack at the sensor. Another salient aspect may be that the number of random projections (i.e., a compressed sensing bandwidth) may be adapted according to channel conditions.

Compressed Sensing Based Acquisition and Reconstruction

Figure 26:
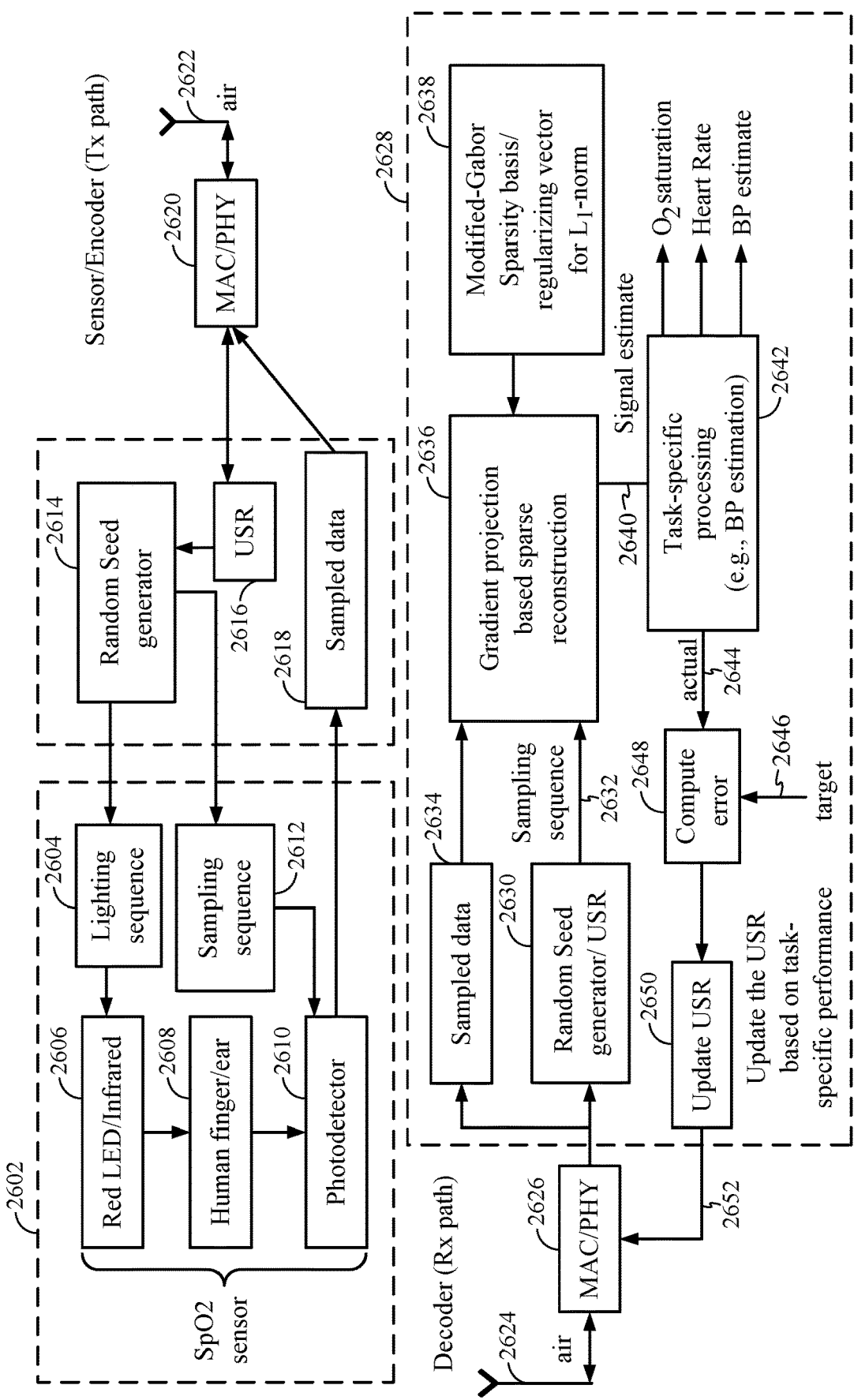
FIG. 26 illustrates an example block diagram of a sensor and a re-constructor in accordance with certain aspects of the present disclosure.

FIG. 26 illustrates an example block diagram for sensing and reconstruction of biomedical signals. A sensor 2602 for acquiring biomedical signals, such as a PPG signal, may comprise three main components: LEDs 2606, a photo-detector 2610, and lighting and sampling sequence for LEDs and photo-detector 2604 and 2612, respectively. The LEDs 2606 may emit light with wavelengths between 600 nm and 1000 nm, which also comprises red and infrared parts of the spectrum. The light from the LEDs 2606 may be transmitted/reflected from a tissue 2608 (e.g., a human finger or ear, as illustrated in FIG. 26) and may be collected on the photo-detector 2610. The ratio of the average intensities corresponding to the LEDs measured at the photo-detector may be useful in determining the oxygen content ($S_pO_2$) in blood. Thus, $S_pO_2$ may be a function of the mean (DC content) of the PPG signal.

The lighting sequence 2604 and the sampling sequence 2612 may be obtained using a random seed generated by a seed generator 2614 according to a defined under-sampling ratio (USR) 2616. The sampled data 2618 from the photo-detector 2610 may be sent for Media Access Control/

Physical Layer (MAC/PHY) processing 2620 before transmission. The processed samples may be then packetized and transmitted by one or more antennas 2622.

At a receiver side, as illustrated in FIG. 26, the transmitted samples may be received at one or more antennas 2624 and processed by MAC/PHY block 2626. The data may be then passed to a re-constructor 2628 for obtaining the originally sensed biomedical signal. For the accurate reconstruction, a random seed generator 2630 that generates a sampling sequence 2632 may need to be synchronized with the random seed generator 2614 of the sensor.

In one aspect of the present disclosure, a gradient based sparse reconstruction 2636 may be applied on sampled data 2634 by using, for example, a modified-Gabor sparsity basis regularizing vector for $l_1$-norm 2638. An estimated signal 2640 may be then utilized by unit 2642 for task-specific processing in order to obtain, for example, a blood pressure estimate, a level of the oxygen in blood, and a heart rate. An actual signal 2644 may be compared with a target signal 2646 by unit 2648 in order to update USR utilized for generating sampling instances. An updated USR value 2652 at the output of unit 2650 may be used by the random seed generator 2630, and may be also fed back to the sensor for adapting the USR 2616 of the sensor. Beside the USR, additional feedback information may be also transmitted to the sensor for adapting some other parameters, such as: a number of measurements at the sensor, coefficients of a measurement matrix, a number of transmitted samples of the signal, and a number of samples in each transmitted packet.

Modulations in the PPG waveform (associated with either red or infrared LEDs) may be related to the instantaneous blood flow. Instantaneous heart rate (HR) may be estimated as the inverse of the distance between waveform peaks. The lighting sequence for the LEDs may depend upon the desired sampling rate for the PPG signal. It may be assumed a uniform Nyquist sampling rate. Also, it can be noted that frequent lighting of the LEDs may result in significant power consumption of the pulse oximeter sensor.

Certain aspects of the present disclosure support exploiting the sparse nature of the PPG signal and making fewer measurements in order to save the sensor power. A Gabor basis may be employed as the transform space consisting of various cosine waves with time support limited by Gaussian window functions at different scales.

Let the original sampled PPG signal be denoted by N-dimensional vector x and the sparse-domain transform basis be represented by N×N matrix W. The (i, j) entry of matrix W may be given as:

$$[W]_{i,j} = \cos\left(\frac{2\pi(i-1)(j-1)}{2N}\right) \times \exp\left(-\frac{(i-1)^2(j-N/2)^2}{wN^2}\right). \quad (1)$$

The term w from equation (1) may be associated with the width of the Gaussian kernel in the Gabor basis. Each row of the matrix W may be normalized such that the corresponding $l_2$-norm is equal to 1, and the matrix W may be referred as the sparse-basis. The PPG signal x may be projected on the sparse-basis to generate the corresponding N-dimensional representation in the Gabor transform space and it may be given as:

$$y = W \cdot x \quad (2)$$

Figure 10:
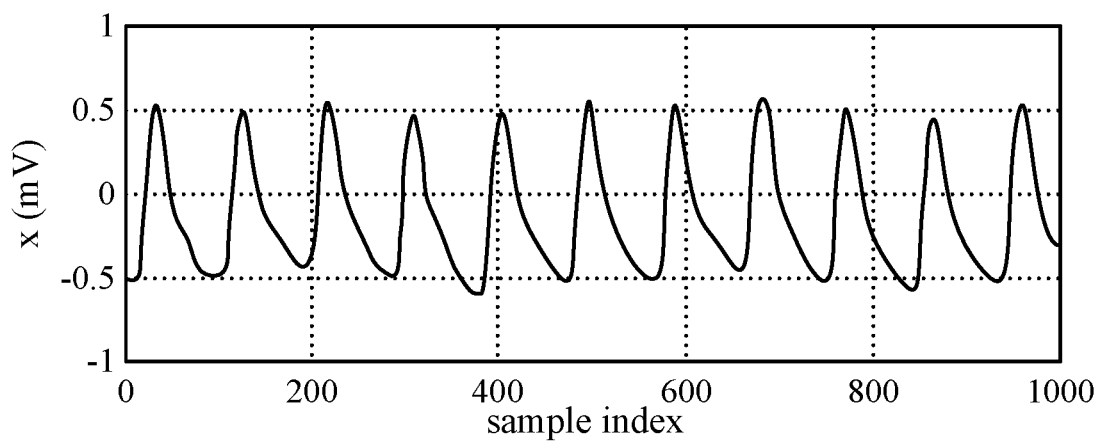
FIG. 10 illustrates an example of a PPG signal and its transform in the Gabor space in accordance with certain aspects of the present disclosure.
Figure 10:
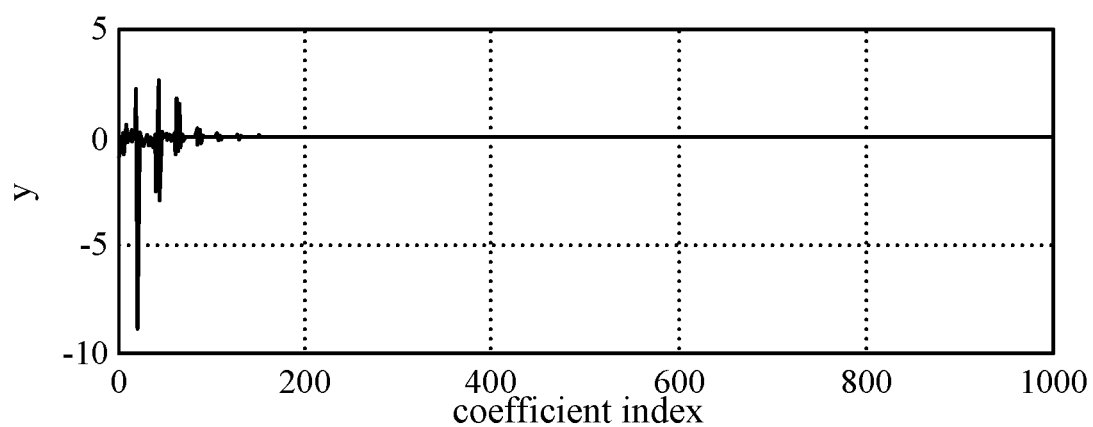

FIG. 10 illustrates an example of a short segment of a PPG signal and a corresponding representation y in the Gabor transform space in accordance with certain aspects of the present disclosure. FIG. 10 illustrates the eight-second segment sampled at 125 Hz (i.e., a total of N=1000 samples). It can be observed that the signal x may be sparse and compressible in the transform domain with about 30 coefficients greater than 0.2 in terms of absolute magnitude. This indicates that most of the PPG signal characteristics may reside in a much lower-dimensional space compared to N and thus the PPG signal may be compressible.

Therefore, the CS principles may be exploited which allows to make K<<N measurements (i.e. to heavily undersample the original data) and still be able to estimate x with a high fidelity. If the signal x is explicitly-sparse with only M non-zero elements in the transform space, then selecting K≥M log N/M samples at random from x may provide sufficient information with a high probability to enable signal reconstruction with zero error.

In real situations, the signal may never be truly sparse and some information content may exist throughout the transform-space. However, the number of significant components with magnitude greater than ε, where ε<<max(y), may be much smaller than N. In FIG. 10, value of ε is 0.2. This approach may be extended to the case where x is not explicitly-sparse, and the CS paradigm may still remain valid. However, the reconstruction error may not be exactly equal to zero.

The sensing process for x may be mathematically expressed. Let P denote a K-dimensional vector containing unique entries (for example, chosen at random) with each element bounded between 1 and N. This may essentially provide K random locations to select the elements from x. The seed for random number generation for constructing the vector P may be generated locally at the sensor or at the receiver. The seed may be based on keys used in security protocols of the communication link. The K-dimensional measurement vector r, obtained from x, may be written as:

$$r = H \cdot x, \quad (3)$$

where H denotes the K×N measurement matrix.

The $i^{th}$ row of the matrix H from equation (3) may be an all-zero vector with 1 at the location given by the $i^{th}$ element of P. It can be noted that in the CS framework the measurement matrix may be defined as a matrix containing random independent and identically distributed (i.i.d) elements. Such a measurement matrix may be necessary when it is not known a priori that the input signal is sparse in the time domain or in the transform domain.

The matching pursuit (MP) algorithm may be employed for signal reconstruction from the measurement vector r. The MP technique represents a greedy algorithm that builds up a signal approximation iteratively by making a locally optimal decision. An initialization of the MP algorithm may be given by defining a modified basis V=H·W of dimension K×N such that V=[$V_1 \ldots V_N$], where $V_j$ is the $j^{th}$ column vector of V. Then, the residual may be initialized as $r_0 = r$, and the approximation ŷ=0 is the same as y (i.e., N). The iteration counter may be also initialized as i=1.

After that, the column vector from V may be found that maximizes the inner-product of the residual $r_{i-1}$ onto V:

$$n_i = \arg\max_{j=1\ldots N} \frac{\langle r_{i-1}, V_j \rangle}{\|V_j\|_{L_2}}. \quad (4)$$

Then, the residual may be updated, and the coefficient vector y may be estimated as follows:

$$r_i = r_{i-1} - \frac{\langle r_{i-1}, V_{n_i} \rangle}{\|V_{n_i}\|_{l_2}^2} V_{n_i}, \quad (5)$$

$$\hat{y}_{n_i} = \hat{y}_{n_i} + \frac{\langle r_{i-1}, V_{n_i} \rangle}{\|V_{n_i}\|_{l_2}^2}. \quad (6)$$

After that, the iteration counter i may be incremented, and $$\Delta_i = \frac{\|r_i\|_{l_2}}{\|r\|_{l_2}}$$

may be defined. If i<m and $\Delta_i$>ε, then the algorithm step defined by equation (4) may be repeated. Otherwise, $\tilde{\Delta}=\Delta_i$ and ĩ=i and the algorithm may proceed to the step defined by equations (5) and (6). Finally, the original estimates may be obtained as $\hat{x}=W\cdot\hat{y}$.

The term m represents the upper-bound on the number of iterations allowed for reconstruction, and the term s defines the convergence criterion. Intuition behind the MP algorithm is twofold. At each iteration step, the algorithm may attempt to find the column of V that may be most strongly correlated with the residual of r, and then may subtract the contribution of this column vector from r. This algorithm is greedy in nature because at each step it may estimate the most dominant component of the original signal x in the projection space W. It can be also noted that the main complexity of the MP algorithm lies in equation (4) which may cost O(K·N) arithmetic operations for a single iteration.

Certain aspects of the present disclosure use the gradient-projection based sparse reconstruction (GPSR) approach to obtain a reconstructed signal from the measurement vector r. This approach may estimate the original signal x by jointly minimizing a data fidelity term (i.e. $l_2$ norm of the error) and the $l_1$-norm in a transform space (i.e. measure of sparsity) under no constraints. It is proposed in the present disclosure to modify this optimization problem by using a weighted $l_1$-norm. The reconstruction algorithm may be given as:

$$\min_K \|Hx - r\|^2 + \tau \sum_{i=1}^N |[f]_i [W \cdot x]_i|, \quad (7)$$

where f is a N-dimensional vector providing the relative importance of coefficients in transform space for computing the measure of sparsity (i.e., $l_1$-norm). The quantity r is a non-negative parameter indicating the relative weight of $l_2$-norm and $l_1$-norm in the cost function. The terms $[f]_i$ and $[W\cdot x]_i$ denote the $i^{th}$ element of vectors f and $[W\cdot x]_i$, respectively.

The $i^{th}$ element of vector f may be given by:

$$[f]_i = \frac{1}{[W \cdot \bar{x}]_i + \sigma}, \quad (8)$$

where σ is a small regularizing parameter. The quantity $\bar{x}$ represents the ensemble mean of the original signal vector x, and may be estimated by averaging training example vectors. A segment from the MIMIC database may be utilized to estimate $\bar{x}$, which can be then excluded from the experimental validations described below.

Figure 25:
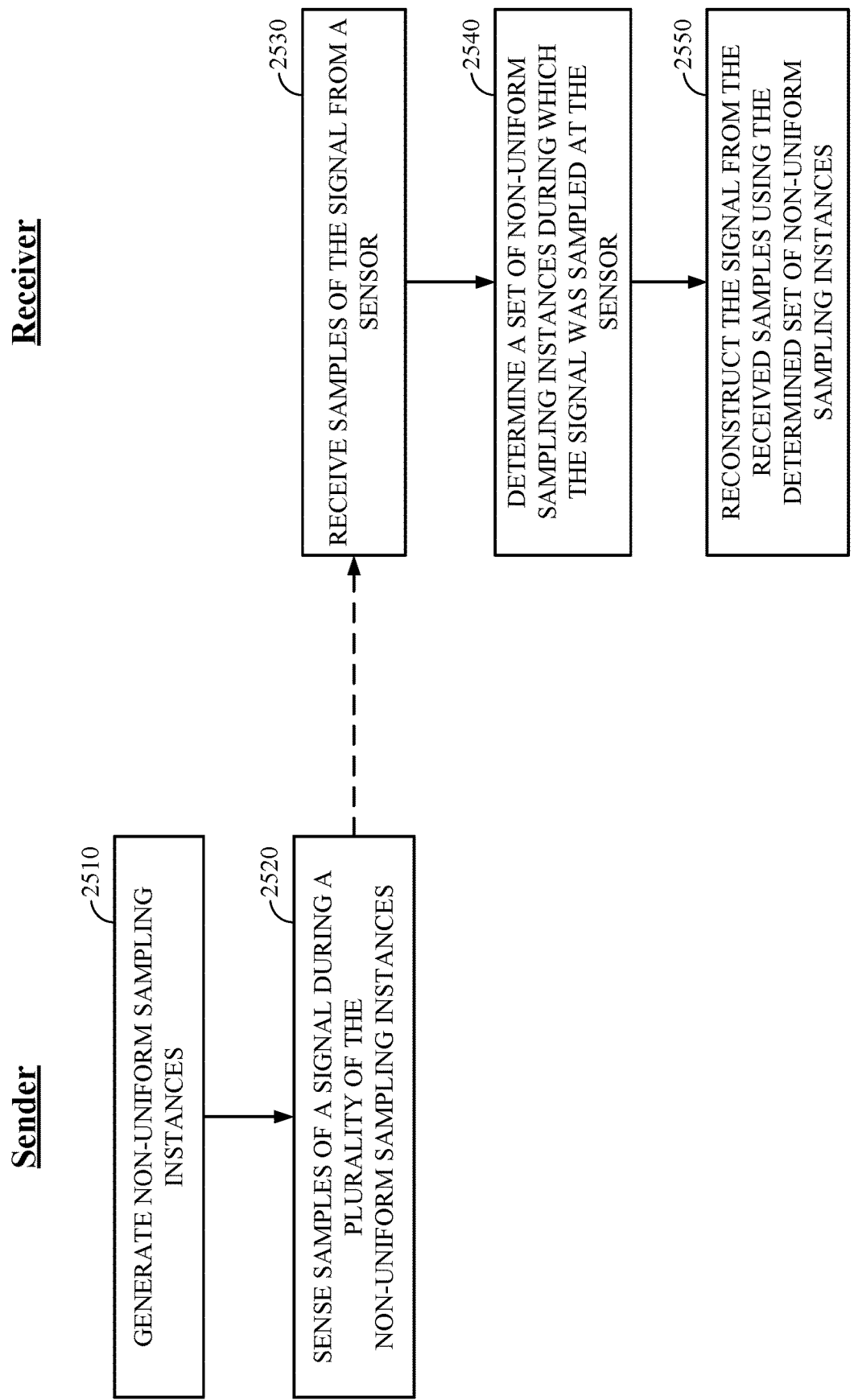
FIG. 25 illustrates example operations for under-sampled acquisition and reconstruction in accordance with certain aspects of the present disclosure.
Figure 25A:
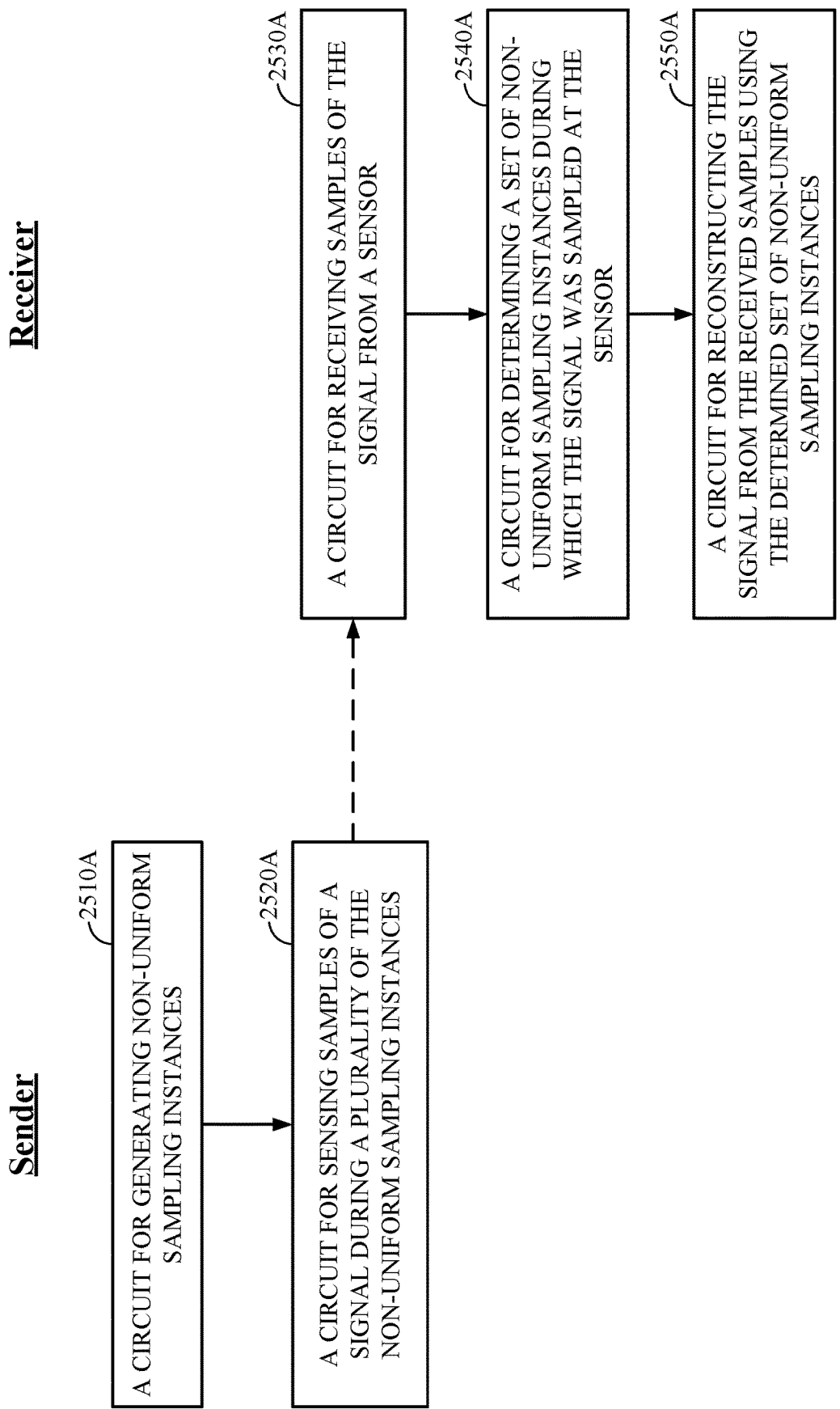
FIG. 25A illustrates example components capable of performing the operations illustrated in FIG. 25.
Figure 28:
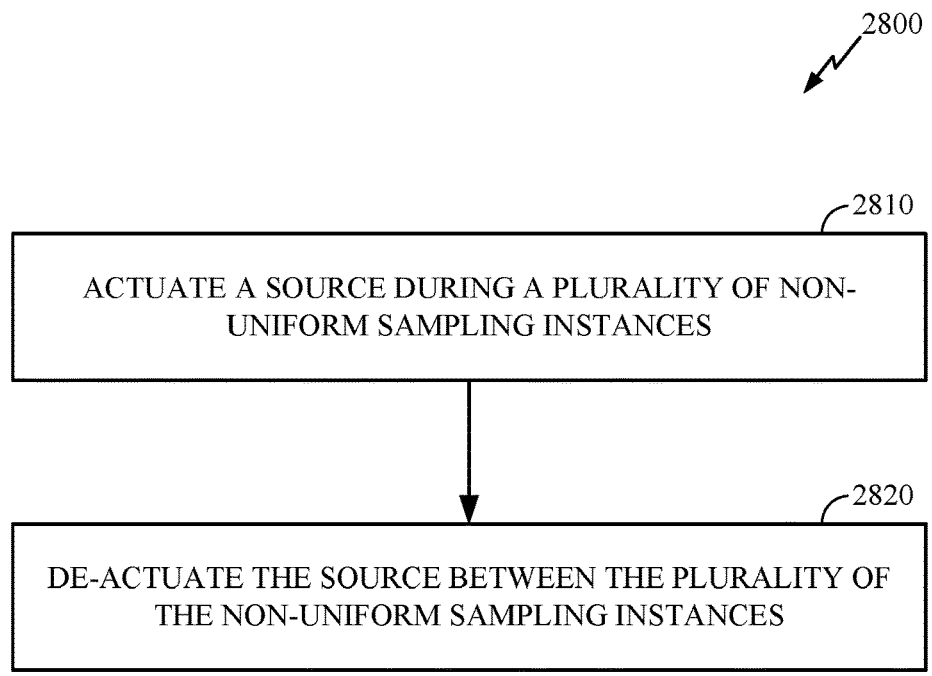
FIG. 28 illustrates example operations for actuating and de-actuating a source at the sensor in accordance with certain aspects of the present disclosure.
Figure 28A:
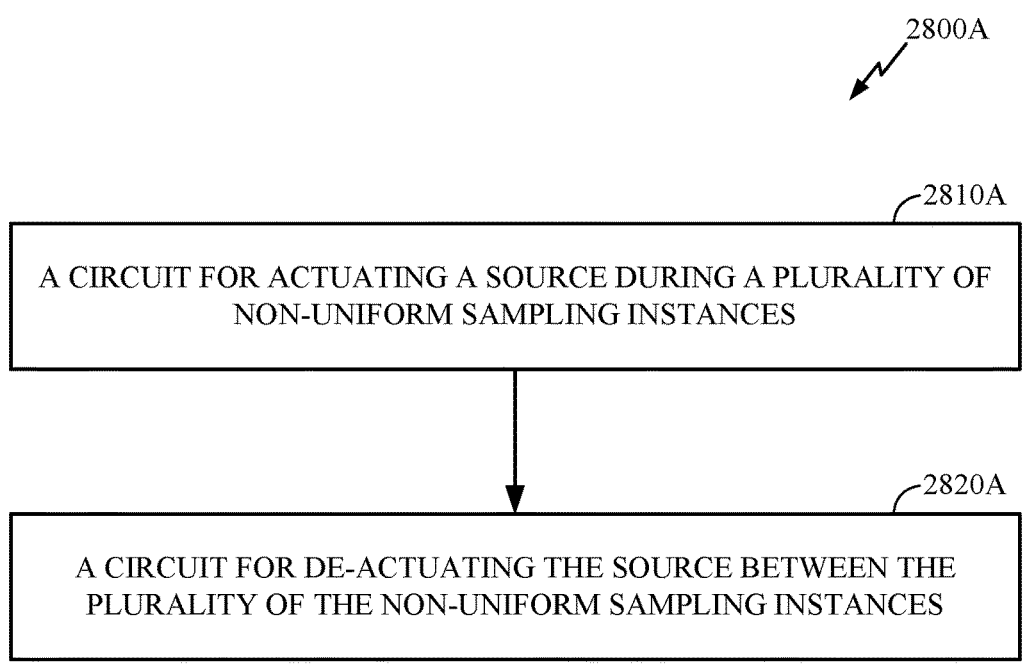
FIG. 28A illustrates example components capable of performing the operations illustrated in FIG. 28.

FIG. 25 illustrates example operations 2500 for under-sampled acquisition at a sensor and reconstruction at a receiver in accordance with certain aspects of the present disclosure. FIG. 28 illustrates example operations 2800 for actuating and de-actuating a light source at the sensor. At 2510, non-uniform sampling instances may be generated at the sensor according to a random seed. At 2520, samples of a signal may be sensed during a plurality of the non-uniform sampling instances. At 2810, the source at the sensor may be actuated, for example, by turning on one or more LEDs during the plurality of the generated non-uniform sampling instances, and the source may be de-actuated, at 2820, between the plurality of the non-uniform sampling instances.

The sensed samples of the signal may be then packetized to obtain at least one packet of the sensed samples, and the obtained at least one packet may be transmitted over a wireless channel. At 2530, samples of the signal may be received from the sensor at a re-constructor. At 2540, a set of non-uniform sampling instances may be determined at the re-constructor during which signal was sampled at the sensor according to said random seed. In one aspect, the seed for non-uniform sampling sequence may be generated at the re-constructor based on keys used in security protocols of a communication link between the sensor and the re-constructor. In another aspect, the seed for non-uniform sampling sequence may be determined at the sensor and conveyed to the re-constructor (i.e., to the receiver). In yet another aspect, the seed for non-uniform sampling sequence may be determined at the receiver and conveyed to the sensor. At 2550, the signal may be reconstructed from the received samples using the determined non-uniform sampling sequence according to, for example, the modified GPSR algorithm defined by equations (7)-(8).

The non-uniform sampling instances may be synchronized with received samples of the signal for accurate reconstruction of the signal. Information observed during the reconstruction (e.g., at least one of: coefficients related to the reconstructed signal, a number of dropped packets during the transmission, a channel signal-to-noise ratio, or the variables $\tilde{\Delta}$ and ĩ) may be utilized to adapt various sensor parameters (e.g., the USR, the number of measurements K, the number of transmitted samples of the signal N, the number of samples of the signal in each transmitted packet P, and the measurement matrix H) by conveying the observed information to the sensor via a feedback mechanism. Then, the non-uniform sampling instances may be adapted at the sensor according to the received feedback information.

Figure 11:
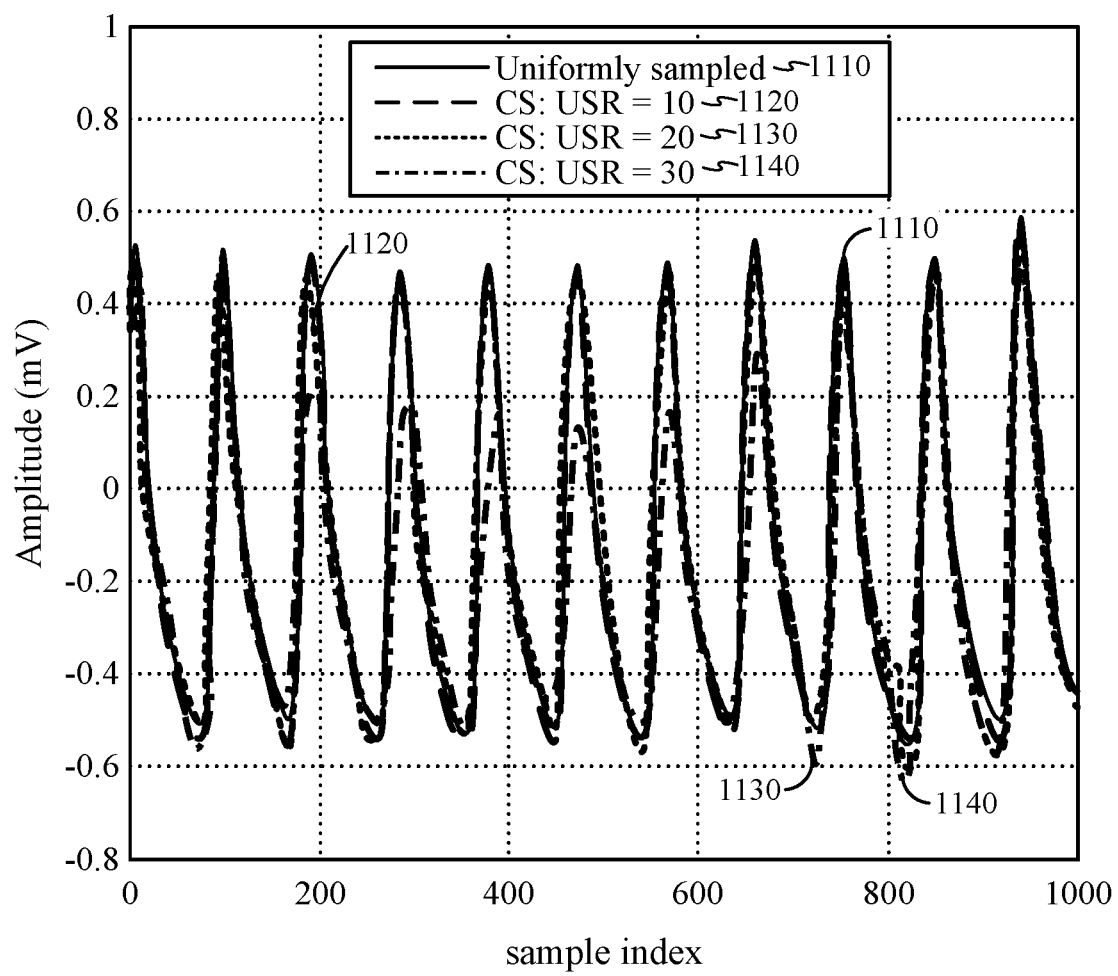
FIG. 11 illustrates a comparison of reconstructed signals obtained using different under-sampling ratios (USRs) in accordance with certain aspects of the present disclosure.
Figure 27:
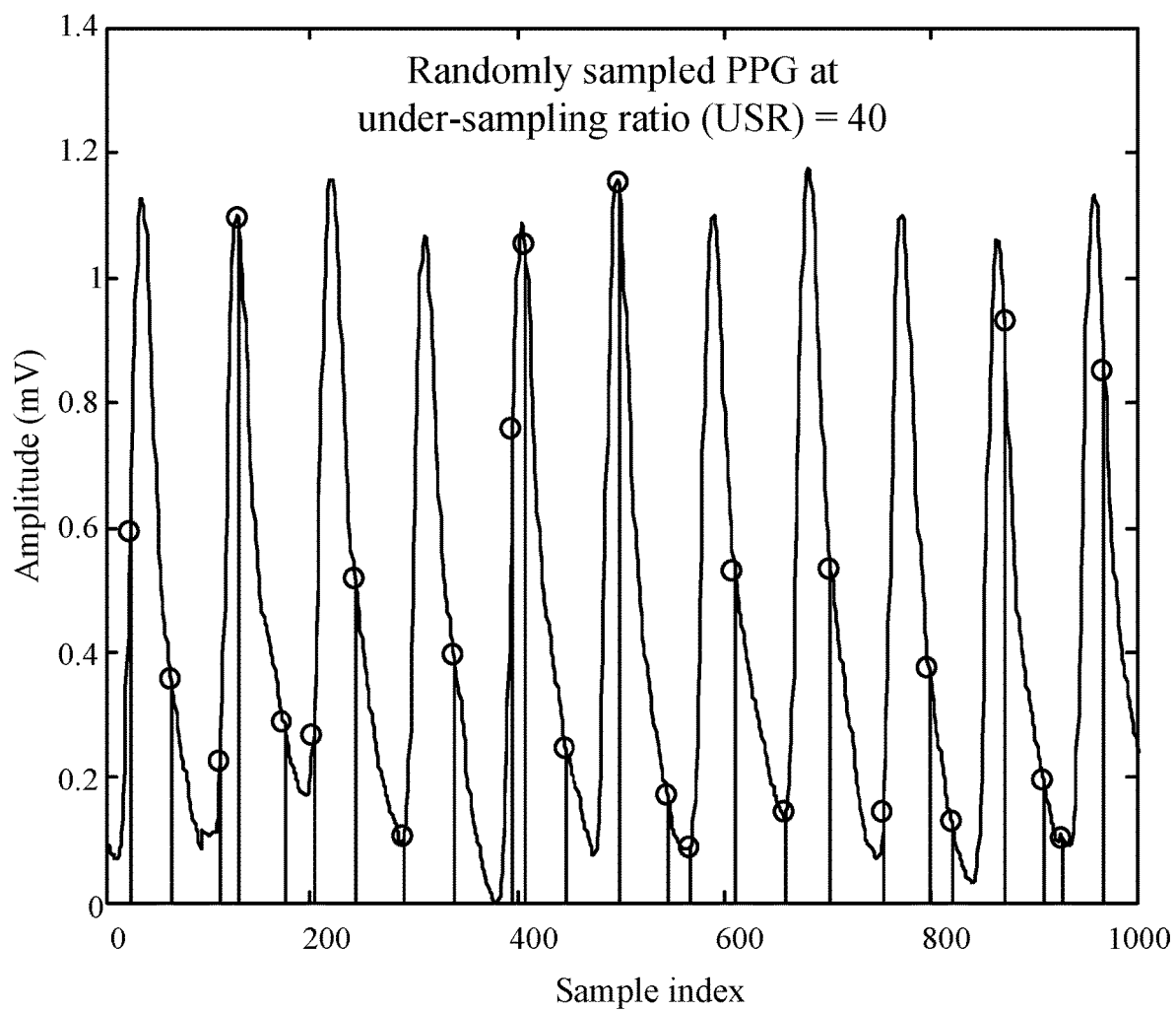
FIG. 27 illustrates an example of a signal sensed at non-uniform sampling instances in accordance with certain aspects of the present disclosure.

Some reconstruction examples generated based on the CS approach are presented in this disclosure. The eight-second segment may be selected from the MIMIC database sampled at 125 Hz (i.e., N=1000 samples). It can be recalled that the number of CS samples is K that defines an under-sampling ratio (USR) as N/K. FIG. 11 illustrates an example for the CS-PPG signal reconstructions obtained for the USR of 10, 20 and 30 with the upper bound on the number of MP iterations m equal to 500. The curve 1110 represents the uniformly sampled original signal and curves 1120, 1130 and 1140 represent reconstructed signals for values of USR of 10, 20 and 30, respectively. FIG. 27 illustrates an example of the signal sensed at non-uniform sampling instances at the USR of 40. The sampling instances are shown as vertical lines.

It can be observed from FIG. 11 that the signal integrity may be well preserved until the USR of 20, and may start degrading thereafter. However, it can be noted that the signal peak locations may be well preserved even with high USR (i.e., the USR value of 30). In this case, the LED power consumption (as a part of the PPG data acquisition) may be significantly reduced by the factor of USR because the LEDs may be lightened for much smaller duration, specifically for only $T \cdot f_s/USR$ seconds instead of $T \cdot f_s$ seconds.

Heart Rate and PPG Reconstructions

It can be recalled from equations (1) and (2) that each element of the coefficient vector y may approximately represent the strength of a cosine (with specific frequency) in a sampled signal x. It can be also noted that a PPG signal may be oscillatory in nature with the dominant frequency being proportional to an HR signal. Therefore, the HR signal may be estimated from the CS reconstruction ŷ, which may be obtained via the MP algorithm, as:

$$\hat{H}R = 60 \cdot (n_{max} - 1) \cdot \frac{f_s}{2N} bpm, \quad (9)$$

where $$n_{max} = \arg\max_{j=2...N} [\hat{y}]_j, [\hat{y}]_j$$

is $j^{th}$ element of vector ŷ, and bpm represents unit of beats per minute.

It can be noted that the HR estimate given by equation (9) may be an average obtained over the time duration of $N \cdot f_s$ seconds. Also, the resolution of the estimate may be given by $$\frac{60 f_s}{2N}.$$

bpm, which is equal to 3.75 bpm for N=1000 and $f_s$=125 Hz. It can be observed that this resolution may be improved with smaller N, and the choice of N=1000 is arbitrary.

The complexity of the MP algorithm for the HR estimation can be compared with the complexity of PPG reconstruction. It can be considered the example PPG signal segment illustrated in FIG. 10, for which $n_{max}$ is equal to 23 implying that the estimated HR is 82.5 bpm. Also, it can be recalled that the MP algorithm is greedy in nature which implies that dominant components of the PPG signal in projection space W may be estimated in the initial iterations. In this case, the two most dominant components may be the DC component and the cosine with frequency corresponding to the HR. Therefore, it can be expected to achieve a reliable estimate of the HR within a few iterations of the MP algorithm, which also suggests that there may be no need to generate an intermediate representation of the complete PPG signal.

On the other hand, it may be required to reconstruct more coefficients in the projection space W for signal reconstruction task, which may result in significantly more iterations of the MP-based post-processing. It can be noted that m iterations of the MP algorithm may roughly cost $O(m \cdot K \cdot N)$ arithmetic operations. Therefore, the HR estimation (e.g., from the CS measurements) may require less computational complexity at the receiver when compared to the PPG signal reconstruction. Also, it can be recalled that the number of CS samples corresponding to the N-dimensional signal x may be K, which defines an under-sampling ratio (USR) as N/K. With increased USR, it can be expected increased computational complexity at the receiver in order to achieve a specified performance level. This represents a trade-off between a sensor power (fewer measurements at the transmitter) and an aggregator power (more iterations and computation at the receiver).

The performance metrics for the HR estimation and the PPG signal reconstruction can be introduced. For the HR estimation, the metric may be a root-mean-square-error (RMSE) defined as $\sqrt{E[\|HR - \hat{H}R\|^2]}$. The metric for the PPG reconstruction may be a normalized RMSE defined as $$\frac{\sqrt{E[\|x - \hat{x}\|^2]}}{\max\{|x|\}}.$$

The term $E[\cdot]$ denotes the expectation operator with Monte-Carlo averaging over various realizations of the PPG signals x and different measurement bases H. The PPG signal realizations x may be taken from the MIMIC database. The true heart rate may be extracted from the original signal x as suggested in equation (9). Each signal segment x may be taken to be 8 seconds long and sampled at 125 Hz.

Figure 12:
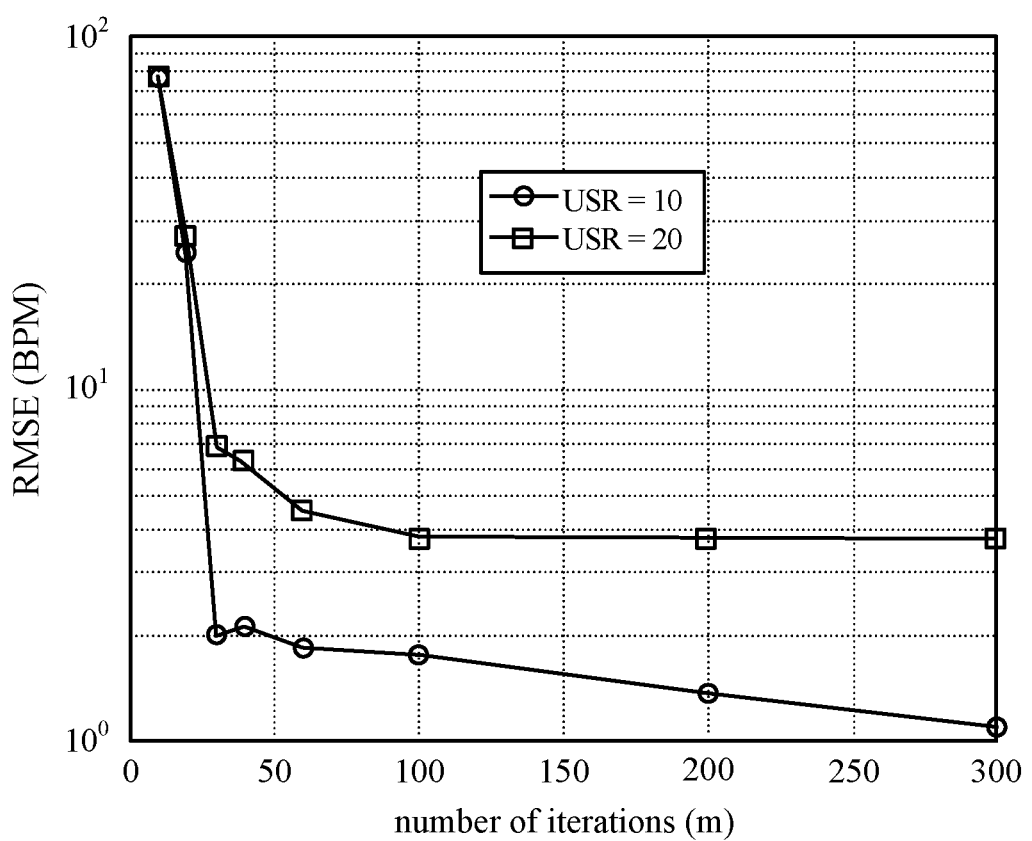
FIG. 12 illustrates a comparison of a heart rate (HR) estimation based on a compressed sensing (CS) framework for different USRs in accordance with certain aspects of the present disclosure.

FIG. 12 illustrates the HR estimation RMSE with respect to a number of iterations m for the MP-based post-processing for the USR of 10 and 20. It can be observed that the RMSE may decrease with increasing m as the estimation accuracy improves with increasing number of iterations. Also, the number of iterations required to achieve a specified RMSE may increase with increasing USR. It can be noted that at m=50, the HR estimation RMSE equals to 1 bpm, which is less than the considered resolution of 3.75 bpm and 4 bpm for USR of 10 and 20, respectively.

Therefore, in order to achieve the HR estimation RMSE of 1 bpm at USR of 10, it may be required roughly on the order of 0.625 million arithmetic operations per second (i.e., $O(m \cdot K \cdot N)$·

$$\frac{f_s}{N},$$

where $f_s$=125 Hz). Similarly, for reconstructing the signal with an RMSE 0.1 at USR=10, it may be required roughly on the order of 3.875 million arithmetic operations per second (i.e., $O(m \cdot K \cdot N + N^2)$·

$$\frac{f_s}{N}).$$

This suggests that the described estimation approach may be handled by computational resources in current smart phones or PDAs.

Figure 13:
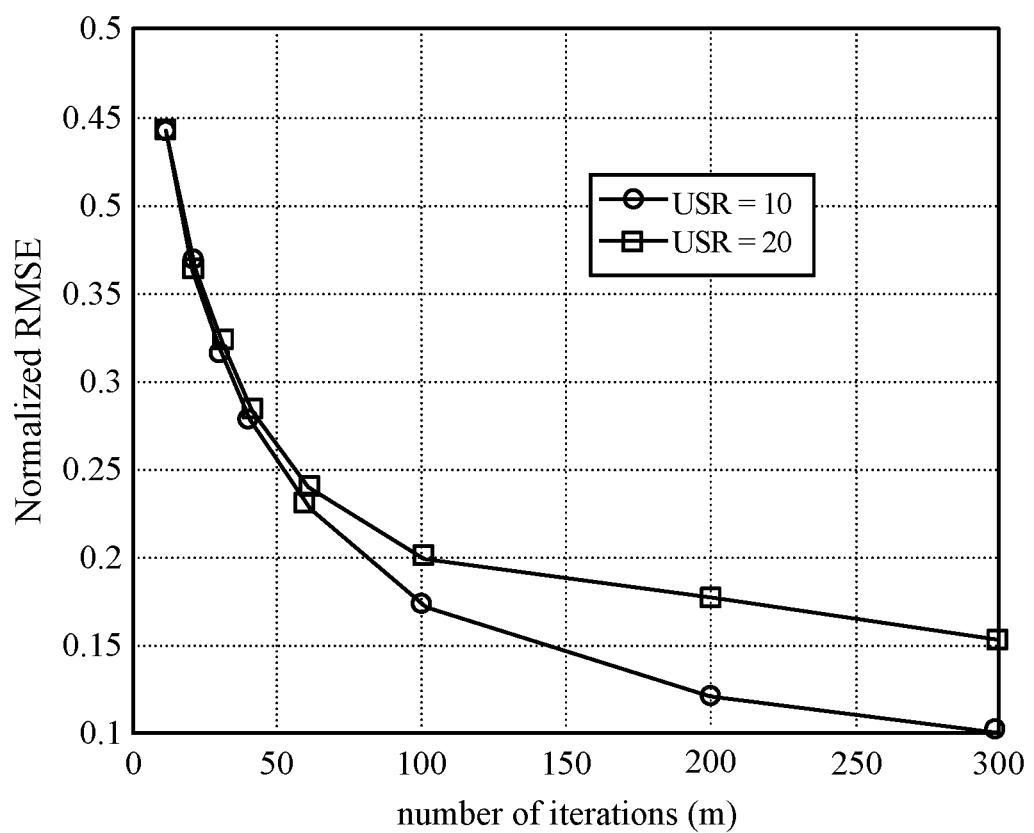
FIG. 13 illustrates a comparison of PPG signal reconstruction based on the CS framework for different USRs in accordance with certain aspects of the present disclosure.

FIG. 13 illustrates a normalized reconstruction RMSE with respect to a number of algorithmic iterations m for the USR of 10 and 20. It can be observed that the RMSE may be reduced with increasing m. However, it can be noted that the decrease may be gradual with m as opposed to the HR estimation RMSE. This may be because the reconstruction task may require estimation of a plurality of coefficients in the sparse space W as opposed to a single dominant component in the case of HR estimation.

Therefore, the receiver complexity may depend upon value of USR, the task of interest and desired performance level. The intermediate representation of the PPG signal (which may require full reconstruction) may not be required for certain tasks, such as the HR estimation task. Furthermore, one could monitor values of 4 and ĩ variables defined in the MP algorithm during reconstruction. This information may be used to modify the value of USR at the sensor side to adapt to signal variations.

Cuffless Blood Pressure Estimation

Figure 14:
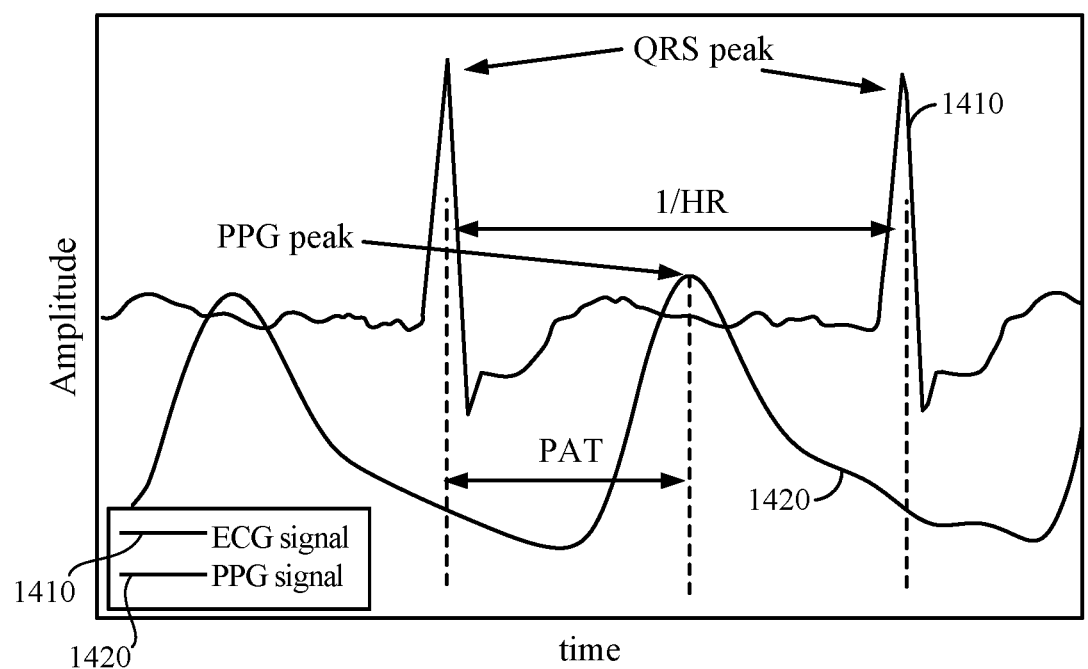
FIG. 14 illustrates an example measurement of a pulse arrival time (PAT) and the HR based on ECG and PPG signal peaks in accordance with certain aspects of the present disclosure.

An SBP and a DBP may be estimated using a pulse arrival time (PAT) and a heart rate (HR), where the PAT can be defined as a delay between a quasi-random signal peak in an ECG waveform and a corresponding peak in a PPG waveform. FIG. 14 illustrates the definition of PAT and HR based on example ECG and PPG waveforms.

The first step involved in a blood pressure (BP) estimation algorithm may be to segment the ECG and PPG signals such that the peaks and other points of interest may be extracted from the signals. The second step may be to estimate the BP from the PAT and from the HR.

The ECG segmentation may be accomplished by applying a band-pass filter between 8 Hz and 15 Hz, followed by squaring and then processing in segments of variable duration. The initial segment duration may be 2 seconds. For every segment, a threshold may be computed and all peaks above the threshold may be located. Then, all peaks less than 0.17 seconds apart may be removed, always maintaining the peak with the highest amplitude. In order to segment the PPG signal, the segment between two consecutive ECG peaks may be analyzed. The peaks and valleys may be detected by finding maximum and minimum points within each segment. In order to provide reliable PAT and HR estimates at any instant, signal peaks in the vicinity may also need to be reliable.

The BP estimation model may be stated as follows:

$$SBP = a_1 \cdot PAT + b_1 \cdot HR + c_1,$$

$$DBP = a_2 \cdot PAT + b_2 \cdot HR + c_2, \quad (10)$$

where calibration parameters $a_i$, $b_i$ and $c_i$, i=1,2 may be estimated during training process and adapted through recursive least squares (RLS) algorithm at every re-calibration opportunity.

In one aspect of the present disclosure, the recalibration may be performed once every one hour. Recalibration duration may essentially imply how often it may be required to estimate or adapt the model parameters. The recalibration step may be required for real applications in order to tackle with bias and drift issues. It may be desired that the re-calibration period is long, so that a blood pressure may be measured continuously and non-invasively in a cuff-less manner for longer periods of time. More frequent recalibrations may reduce the BP estimation error whereas less frequent recalibrations may make the system more amenable for everyday use.

The results of BP estimation using the CS-PPG are presented and compared with those using Nyquist-PPG. For example, records corresponding to 13 patients from the MIMIC database can be used for this evaluation, where length of the records is on average of the order of 38 hours. The gradient projection based sparse reconstruction (GPSR) approach may be used to generate CS-PPG for the entire patient record.

FIG. 15 illustrates the BP estimation results based on the use of ECG and CS-PPG signals of the proposed approach. The value of USR can be taken to be 40 for the CS framework-based measurement of the PPG signal. It may be important from the BP monitoring perspective to compute the frequency of reporting/generating BP estimates. The term $N_{BP}$ can be introduced as the average number of BP estimates generated per minute using the CS-PPG and the Nyquist-PPG baseline algorithm.

FIG. 15 also illustrates the standard deviation of the SBP and DBP estimation error, as well as $N_{BP}$ for the Nyquist-PPG and for the CS-PPG with USR of 40. The Association for the Advancement of Medical Instrumentation (AAMI) requirements for BP estimation indicates that the standard deviation of the error has to be below 8 mmHg, both for the SBP and the DBP. It can be observed from FIG. 15 that the average standard deviation for both SBP and DBP estimation error may be less than 8 mmHg. Furthermore, the accuracy does not degrade by using the CS-PPG when compared to the Nyquist-PPG. In this exemplary simulation, an average of 8.85 BP measurements per minute may be estimated at USR of 40, compared with an average of 51 BP estimates per minute using Nyquist-PPG.

The CS-based low power solution is proposed in the present disclosure for acquiring the PPG signals, while the HR and the BP estimation accuracy may not be compromised using the proposed CS-PPG approach. It is also demonstrated that the entire PPG signal may be reconstructed with arbitrarily fine resolution, provided that at least K≥M log N/M samples are acquired and an adequate computational resources are available at the receiver.

Compressed Sensing Based Packet-Loss Concealment

The issue of packet losses due to poor channel conditions, congestion and mobility between a sender and a receiver is addressed in this disclosure. It can be particularly interesting to exploit the sparse nature of biomedical signals (i.e., PPG signals, ECG signals, etc.) in order to improve robustness against packet losses in a communication link. When a signal being transmitted over the air is sparse in nature (i.e., it has redundancies), then packet-losses may be loosely treated as compression performed by a channel.

Figure 17:
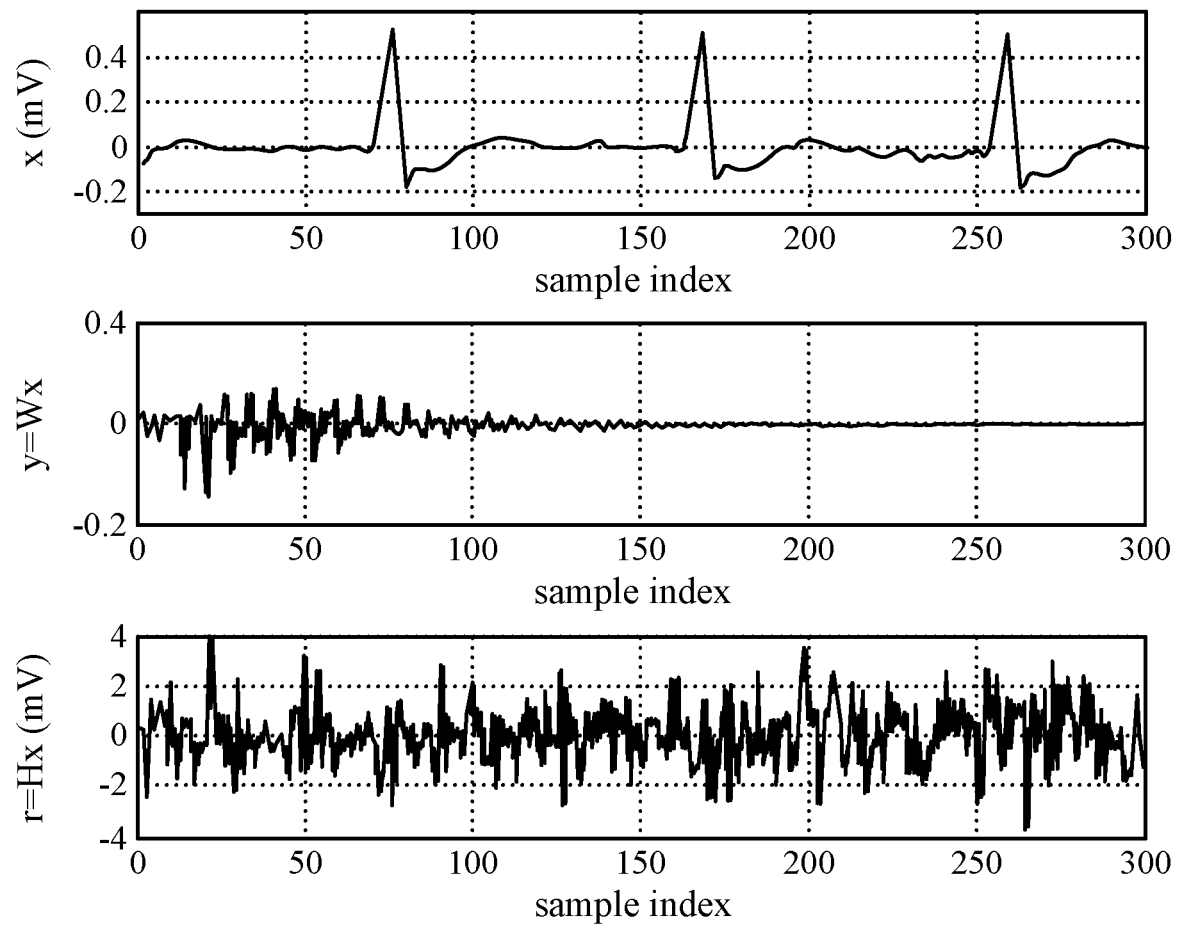
FIG. 17 illustrates an example ECG signal, its transform in the Gabor space and a precoded version of the ECG signal in accordance with certain aspects of the present disclosure.

Certain aspects of the present disclosure support a CS-based approach to lower the power consumption and to achieve robust communication of the ECG signals in telemedicine. It can be observed that the ECG signals may be less sparse in the Fourier/Gabor space compared to the PPG signals. As illustrated in FIG. 17, there may be many components within the 0.05 Hz to 40 Hz band, which may be considered clinically relevant for the ECG signals. The CS-based PLC approach proposed in the present disclosure may also be completely applicable to the PPG and other signals, provided at least K≥M log N/M measurements are available at the receiver for reconstruction.

It can be assumed that data may be wirelessly transmitted in the form of packets from the sender (i.e., sensor) to the receiver (i.e., aggregator). Following traditional terminology, each packet may contain a Service Data Unit (SDU) and an Application Data Unit (ADU). The ADUs may contain the ECG payload of the application layer, and payload may be defined to contain P ECG samples with typical bit resolution of 8 to 12 bits. It can be assumed that SDUs with channel errors may be dropped in the lower layers, and locations of lost packets may be identified at the application layer via the sequence number field in headers of correctly received packets.

Data may not be transmitted in the form of raw ECG samples. Instead, application layer precoding may be performed on the data. The idea is to pre-code the original ECG signal before transmission by using the random measurement matrix H defined in equation (3). The resulting pre-coded data may be used to form n>1 (i.e., multiple) packets which may be then transmitted to the receiver in sequential order. This operation may ensure that it may be possible to infer some information about the original signal in the case of packet losses. The CS-based reconstruction principle may be applied to the received data in order to obtain the ECG signal estimate, the HR estimate, etc. This process may be analogous to convolutional encoding where each information bit to be transmitted is spread over a longer duration defined as a constraint length. The number of samples in each ADU is denoted by P. The ECG signals may be taken from the MIMIC database and the sampling rate may be $f_s=125$ Hz.

Figure 16:
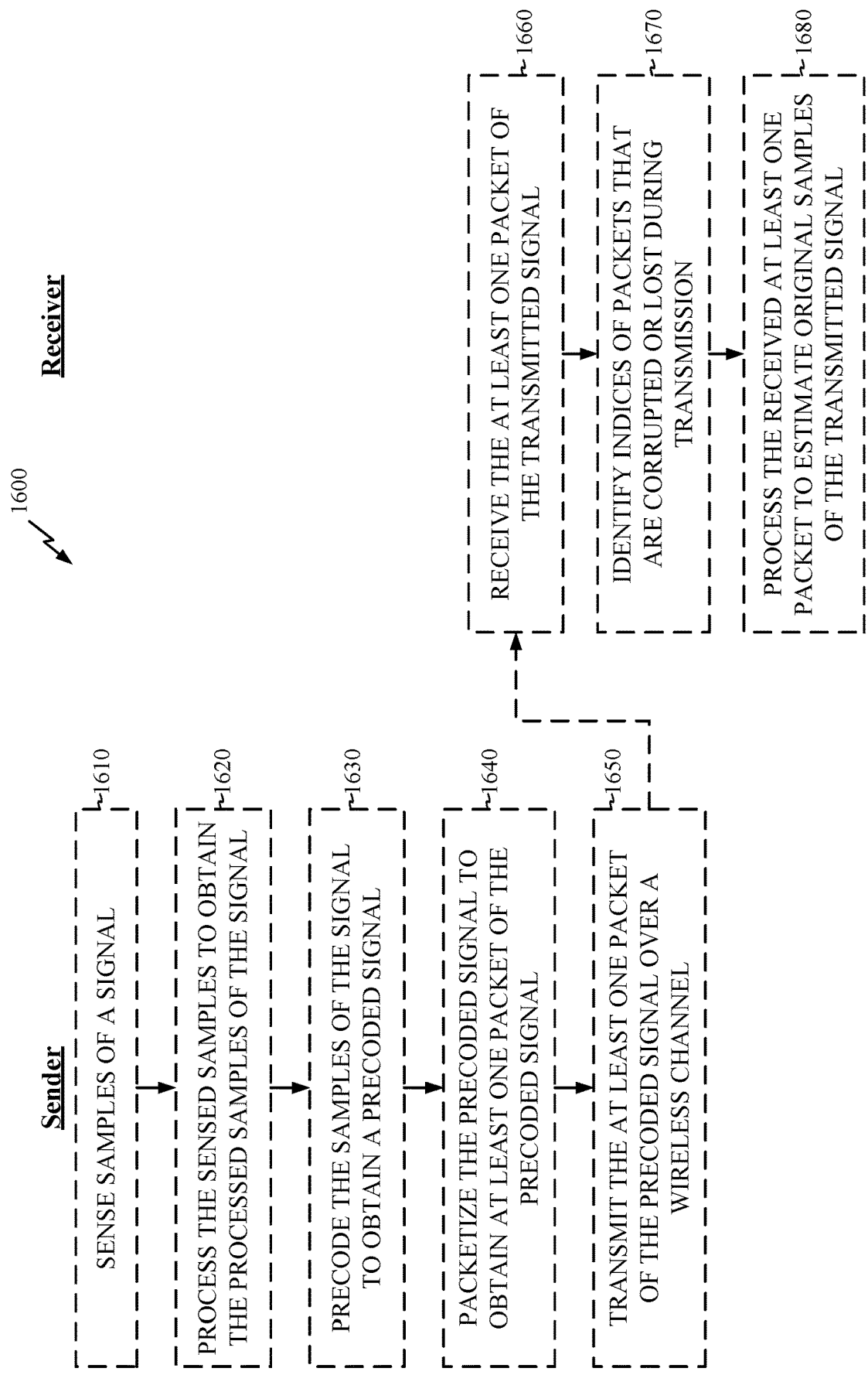
FIG. 16 illustrates example operations for CS-based packet loss concealment (PLC) method in accordance with certain aspects of the present disclosure.
Figure 16A:
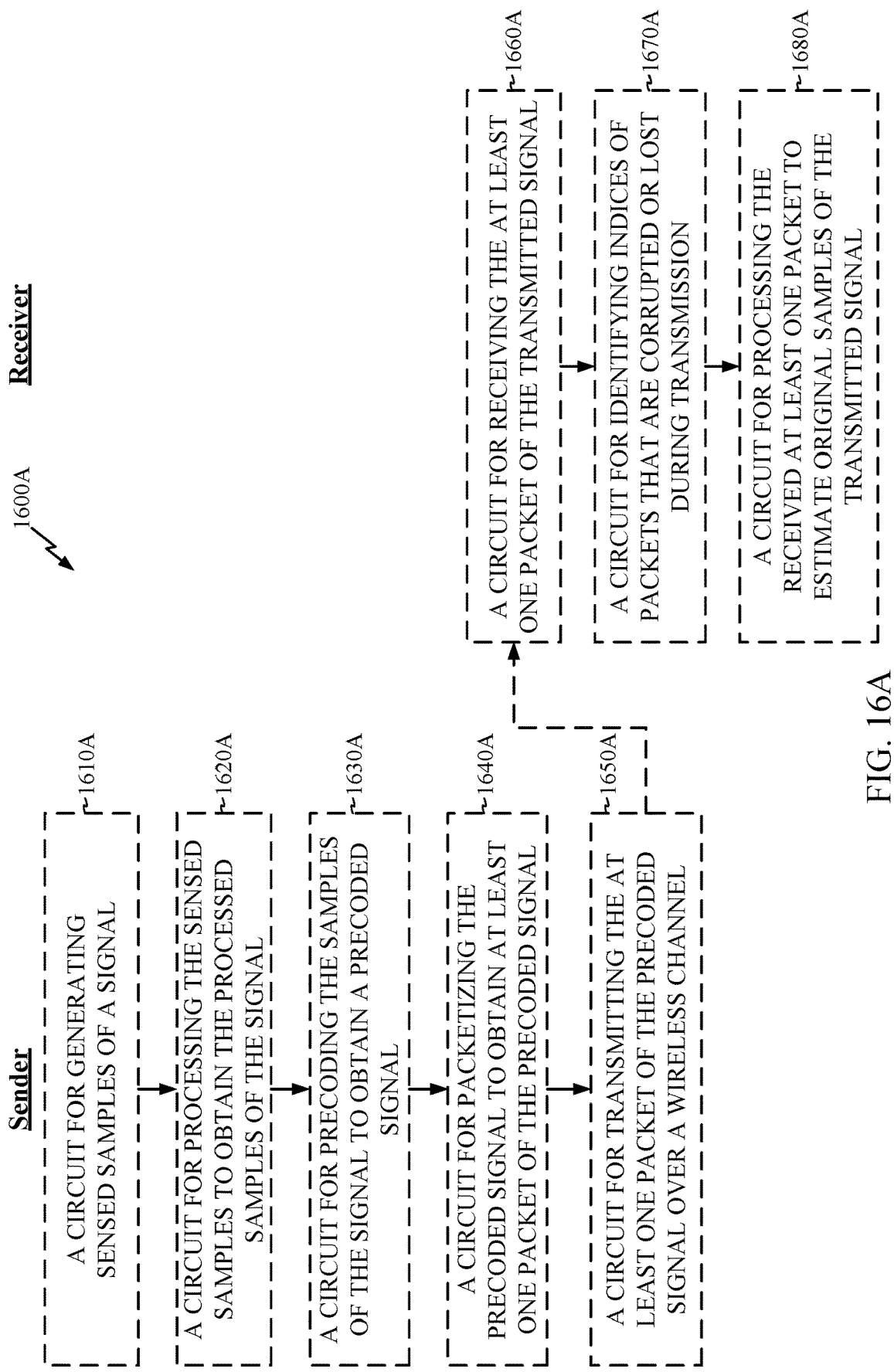
FIG. 16A illustrates example components capable of performing the operations illustrated in FIG. 16.

FIG. 16 illustrates example operations 1600 for CS-based packet loss concealment (PLC) in accordance with certain aspects of the present disclosure. Operations 1610-1640 may be performed at a sender (e.g., a biomedical sensor, such as a PPG sensor and an ECG sensor), and operations 1650-1670 may be performed at a receiver (e.g., a mobile handset or a PDA).

At 1610, samples of a monitored biomedical signal may be acquired. For example, a vector x comprising of the N consecutive ECG samples, where N=n·P may be generated. After that, a measurement matrix H of dimension K×N may be created. In one aspect, the elements of the matrix H may be independently chosen from the symmetric Bernoulli distribution $Pr(H_{i,j}=-1 \text{ or } 1)=\frac{1}{2}$. In another aspect, rows of the measurement matrix may be randomly chosen from $2^K$ Walsh sequences. In yet another aspect, rows of the measurement matrix may be randomly chosen from the Haar matrix of size N×N.

At 1620, the acquired samples of the monitored biomedical signal may be optionally processed to obtain a processed signal of interest. For example, as illustrated in FIG. 14, the ECG and PPG signals may be utilized to obtain a pulse arrival time (PAT) and a heart rate (HR) variability, as well as to obtain an oxygen content in blood. The HR variability and the PAT may be further used to compute a blood pressure, as defined by equation (10). At 1630, either the original signal x (e.g., the ECG signal and the PPG signal) or the processed signal (e.g., the PAT, the HR variability, the oxygen content, etc) may be precoded using the measurement matrix to obtain a precoded signal.

At 1640, the precoded signal may be packetized to obtain at least one packet of the precoded signal. For example, K precoded samples may be packed into n=K/P packets before transmission. If the channel were to drop some packets, then the underlying transform-domain sparsity of the monitored biomedical signal may be used to reconstruct the original signal from the correctly received precoded data packets. It can be noted that the reconstruction fidelity may depend upon the packet loss rate and the signal sparsity structure. At 1650, the at least one packet of the precoded signal may be transmitted over a wireless channel. Because N samples may be precoded and transmitted, a constant end-to-end latency of $$N/f_s \left( \text{or } \frac{n \cdot P}{f_s} \right)$$

seconds may be introduced in the system. The parameter K may be set to N (i.e., to n·P). It can be recalled that for the PPG acquisition, the parameter K may be set much smaller than N and leverage sparsity in order to save an acquisition power.

At 1660, the at least one packet transmitted over the wireless channel may be received at an aggregator. At 1670, indices of packets that are corrupted or lost during transmission may be identified. These indices may be then used to reconstruct original samples of the transmitted signal, at 1680.

The sensor may utilize a random seed to generate a sequence of non-uniform sampling instances. This random seed may be communicated to the receiver, so that the sequence of sampling instances may be re-generated and used during the reconstruction. On the other hand, the receiver may choose a random seed based on keys used in secure communication. In this case, the receiver may inform the sensor which random seed to use, so that identical sequences of sampling instances may be employed at both sensor and receiver.

Let the wireless channel be represented by a diagonal matrix $H_c$ of dimension K×K. Let S be a set containing indices of packets lost and not available at the application layer for reconstruction. The cardinality of the set S may represent the number of dropped packets. The elements in the diagonal of $H_c$ may be defined as follows:

$$[H_c]_{i,i} = \begin{cases} 0 & \text{if } \left\lceil \frac{i}{P} \right\rceil \in S \\ 1 & \text{otherwise} \end{cases} \quad (11)$$

The pre-multiplication of $H_c$ with r may essentially provide the precoded data samples that were successfully received. The resulting vector can be denoted as and it is given by $H_c \cdot H \cdot x$. If the cardinality of set S is n, then this may imply that all the packets were dropped during the transmission, and in this case the estimated signal at the receiver may be set to zero. If the cardinality of set S is zero (i.e., $H_c$ is an identity matrix), then this may imply that no packets were dropped. In this case, the ECG signal $\hat{x}$ may simply be estimated as $H^{\#} \cdot \hat{r}$, where $H^{\#}$ is a pseudo-inverse of H. If the cardinality of S is greater than zero and less than n, then the previously described MP algorithm may be used to obtain the signal estimate $\hat{x}$ based on the received vector $\hat{r}$. It can be noted that the term H in the MP algorithm may need to be replaced by $H_c \cdot H$ in this particular case.

The Gabor basis W defined in equation (1) may be used to enforce sparsity during the CS reconstruction. This particular CS-based PLC scheme may be referred as the CS-PLC. FIG. 15 illustrates an example of a short segment of the ECG signal x and its corresponding representation y (i.e., W·x) in the Gabor transform space. The precoded version of x given by r=H·x is also illustrated in FIG. 17.

It can be noted that the precoding within the CS-PLC approach may involve n·P inner-products and each inner-product may require on the order of n·P arithmetic operations. Therefore, the precoding complexity is on the order of $O(n^2 \cdot P^2)$. In order to decrease the precoding complexity, an alternative CS-based PLC approach based on interleaving is also proposed in the present disclosure.

Figure 18:
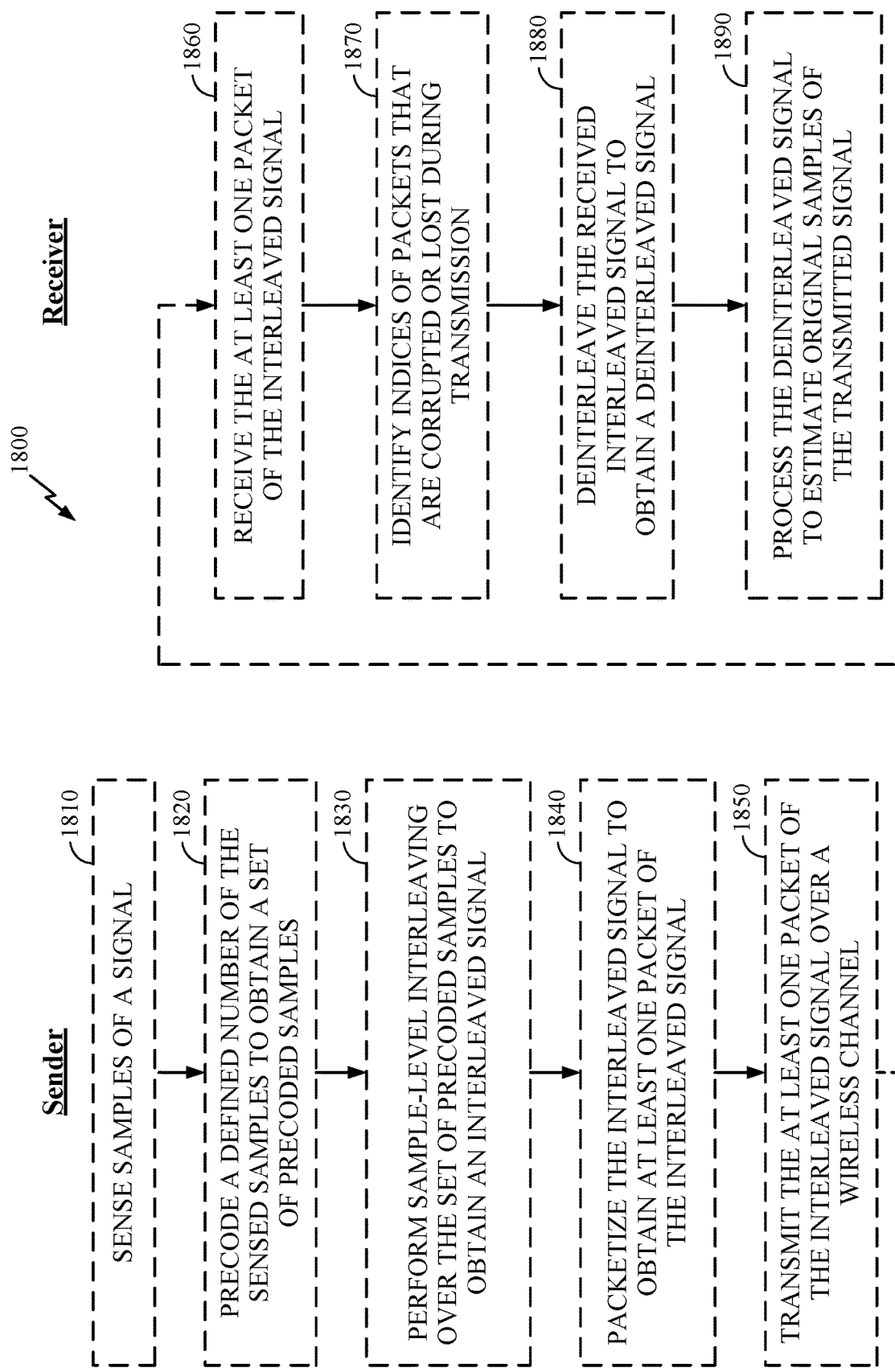
FIG. 18 illustrates example operations for interleaving-based CS-PLC method in accordance with certain aspects of the present disclosure.
Figure 18A:
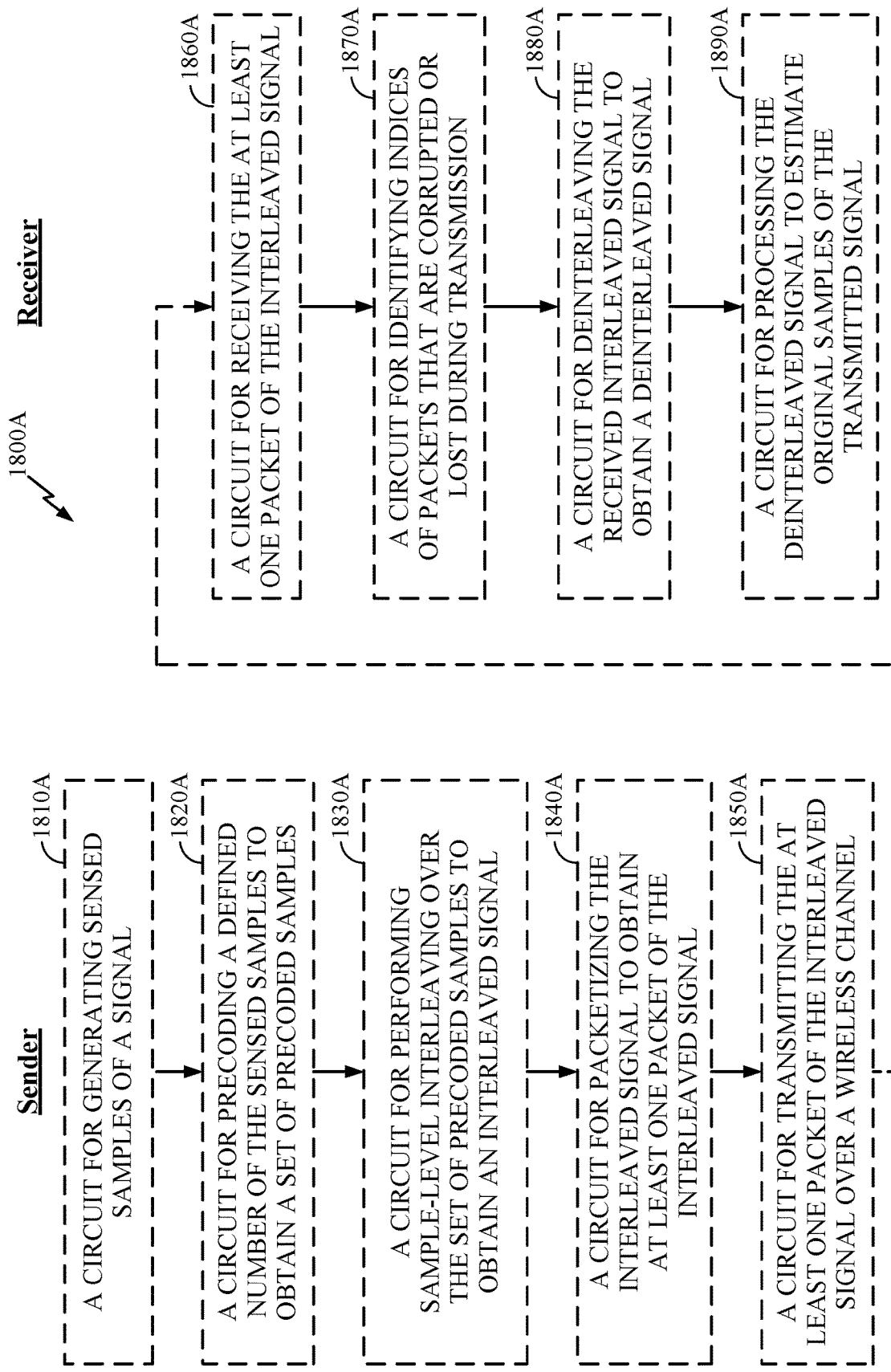
FIG. 18A illustrates example components capable of performing the operations illustrated in FIG. 18.

FIG. 18 illustrates example operations 1800 for interleaving based CS-PLC in accordance with certain aspects of the present disclosure. Operations 1810-1850 may be performed at the sender (e.g., the sensor of a biomedical signal, such as the PPG sensor and the ECG sensor). Operations 1860-1890 may be performed at the receiver (e.g., the mobile handset or the PDA).

At 1810, samples of a monitored biomedical signal may be acquired. At 1820, a defined number of the acquired samples may be precoded to obtain a set of precoded samples. At 1830, a sample-level interleaving may be performed over the set of precoded samples to obtain an interleaved signal. At 1840, the interleaved signal may be packetized to obtain at least one packet of the interleaved signal. At 1850, the at least one packet of the interleaved signal may be transmitted over a wireless channel.

At 1860, the at least one packet transmitted over the wireless channel may be received. At 1870, indices of the packets that are corrupted or lost during the transmission may be identified. These indices may be then used to reconstruct original samples of the transmitted signal. At 1880, the received signal may be de-interleaved to obtain a de-interleaved signal. Finally, at 1890, the de-interleaved signal may be processed, for example by using the MP algorithm, in order to estimate the original samples of the transmitted signal.

The main difference as compared to the CS-PLC scheme 1600 illustrated in FIG. 16 is that the precoding may be now performed for P ECG samples instead of n·P samples, which may reduce the precoding complexity by a factor of $n^2$. This may be followed by the sample-level interleaving of the precoded data across the length of n·P samples. Although the original ECG data may be precoded over shorter durations as compared to the CS-PLC scheme 1600 from FIG. 16, the interleaving step 1830 may allow spreading the signal information across a longer duration. The interleaving process may facilitate handling of bursty channel errors (i.e. losing multiple packets in sequence). It can be also noted that the parameters USR, n, K and H may be adapted based on observed values of $H_c$, $\tilde{\Delta}$ and $\tilde{\imath}$ at the receiver in order to achieve the optimal trade-off between sensor life and reconstruction fidelity.

The proposed CS-PLC scheme can be compared with retransmission-based approach, where up to k−1 retransmission attempts may be made on packets that are not successfully received at the receiver. Therefore, k=1 indicates that the data may be transmitted only once from the sender, and if a packet is dropped then the corresponding signal locations may be set to zero by the receiver. The retransmission may have a smaller bandwidth penalty compared to forward error correction (FEC), but at the cost of considerable complexity at the sensor as packets may need to be buffered at the sender. Furthermore, the system latency may be large, and it is proportional to a round trip time (RTT). For these reasons, the CS-PLC approach may be preferable over FEC and retransmission-based approaches for low power sensors.

Quantitative comparisons of various PLC schemes discussed above are presented with respect to packet loss rate. The packet loss rate may be an indicator of channel conditions, congestion, etc., and it may represent a rate at which packets get dropped during the transmission. The packet loss rate may be bounded between 0 and 1, where 0 may indicate that the channel is clean and 1 may indicate that the channel is completely unreliable. All the comparisons presented in this disclosure are averaged over 20,000 Monte-Carlo channel realizations.

The performance of the PLC schemes is first evaluated in terms of normalized RMSE defined as $$\frac{\sqrt{E[\|x - \hat{x}\|^2]}}{\max\{|x|\}}.$$

The term E[•] denotes the expectation operator with Monte-Carlo averaging over various realizations of ECG signals x and different channel realizations. The ECG signal realizations x may be taken from the MIMIC database sampled at 125 Hz.

Figure 19:
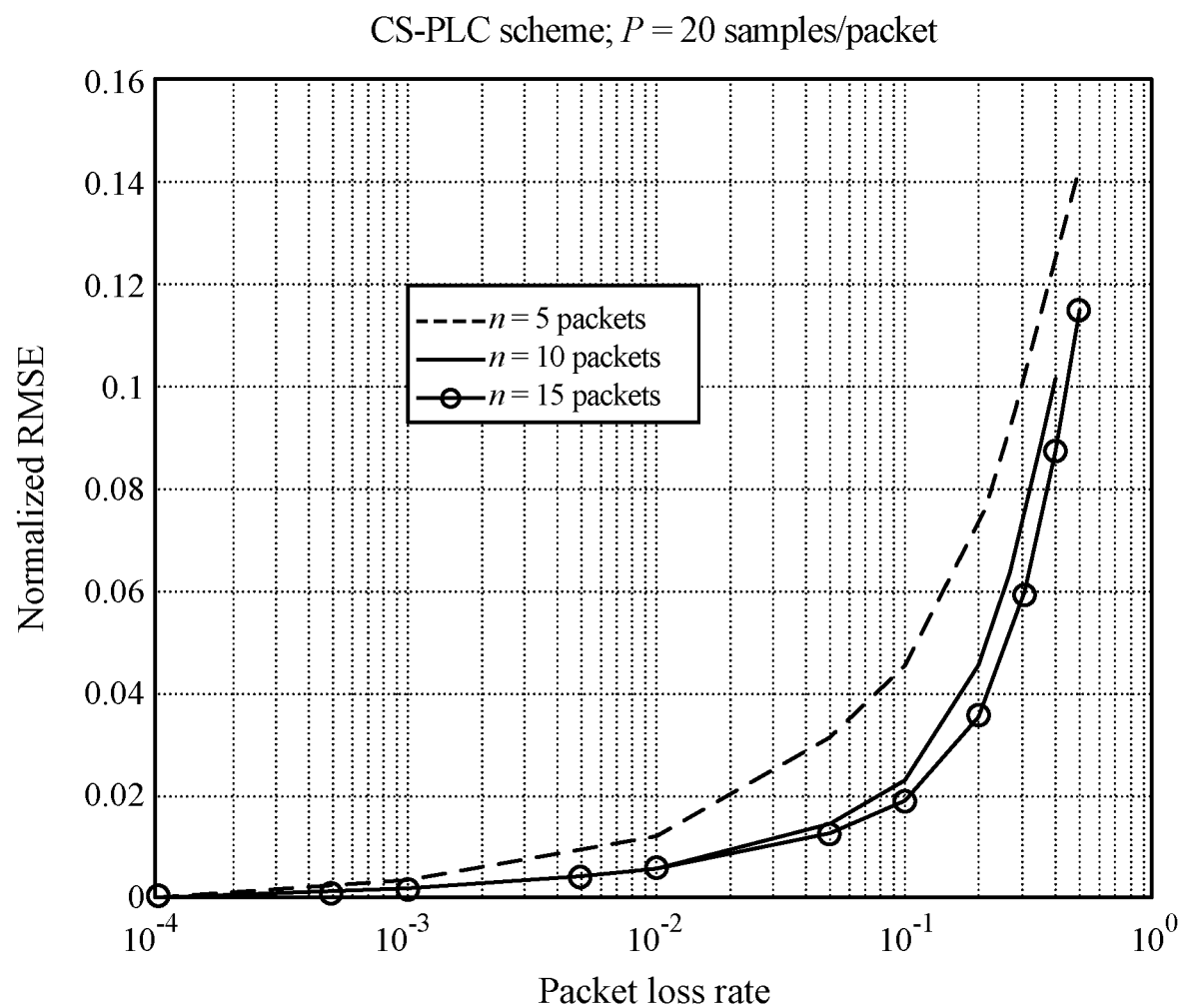
FIG. 19 illustrates a graph of example root-mean-square-error (RMSE) performance of the CS-PLC for different number of transmitted packets in accordance with certain aspects of the present disclosure.

FIG. 19 compares the normalized RMSE performance of the CS-PLC scheme for different values of parameter n. The value of K is set to 20 samples per packet for each presented quantitative analysis. The considered exemplary values of n are 5, 10 and 20 corresponding to latencies of 0.8, 1.6 and 2.4 seconds, respectively. It can be observed from FIG. 19 that normalized RMSE may degrade with increasing packet loss rate. This can be expected because higher packet loss rates may imply reduced amount of reliable data available at the receiver for estimating $\hat{x}$. Also, it can be noted that normalized RMSE performance may improve with increasing number of packets n. With a higher n, the sparsity may be enforced over a longer ECG signal duration and thus the reconstruction fidelity may be improved.

Figure 20:
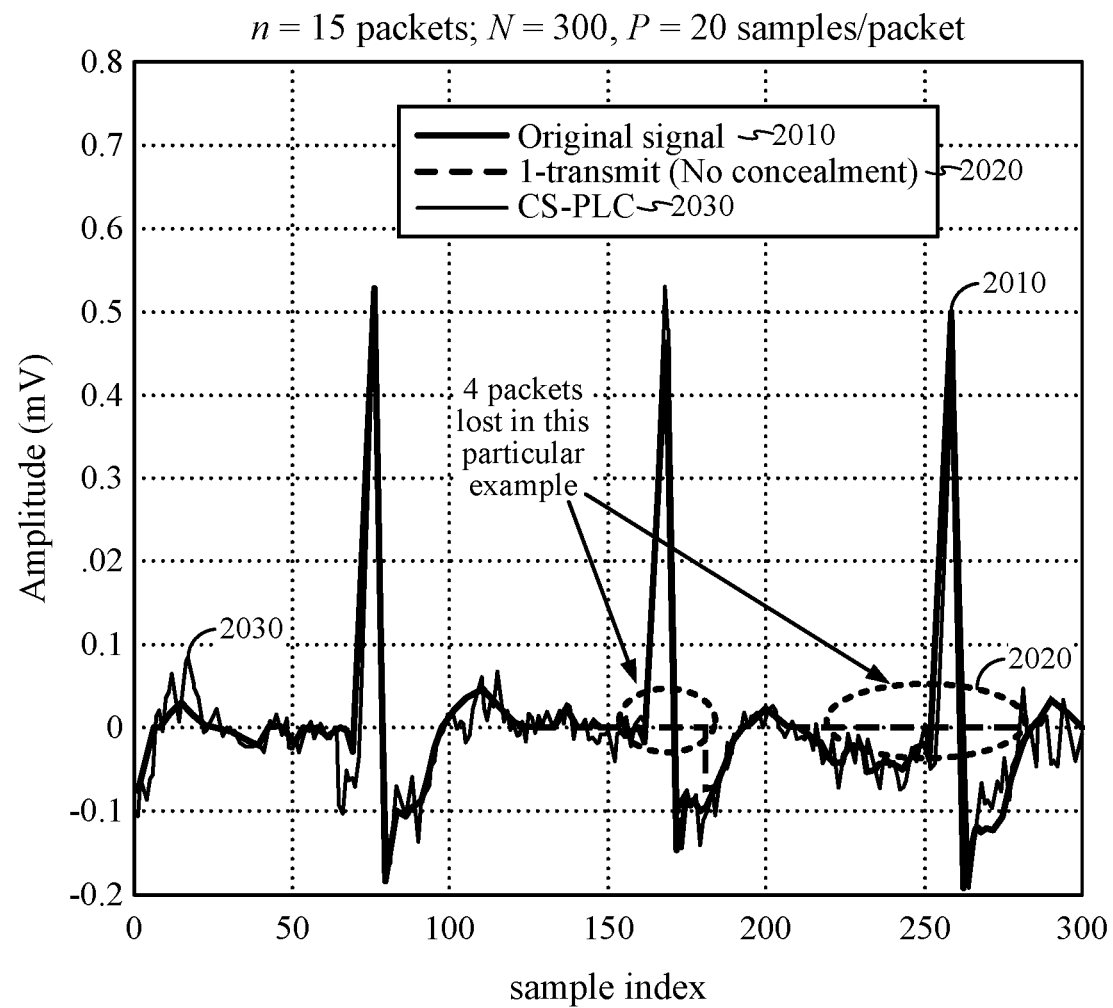
FIG. 20 illustrates an example of signal reconstruction using the CS-PLC approach and a scheme without PLC in accordance with certain aspects of the present disclosure.

FIG. 20 illustrates an example signal reconstruction at the receiver when four packets were dropped by the wireless channel. In this particular example n is set to 15 packets. A curve 2010 represents the original signal. A curve 2020 represents k-transmit scheme, where k=1 (i.e., single transmission), and a curve 2030 represents the CS-PLC-based signal estimate. There is no packet loss concealment involved in the 1-transmit scheme corresponding to the curve 2020, i.e., if a packet is lost then zeros may be substituted in the appropriate signal location at the receiver. It can be noted that with 1-transmit scheme two ECG peaks may be lost in this particular example, whereas using the CS-PLC the complete ECG signal may be estimated with a high fidelity. It can be also noted that losing signal content at critical locations may have severe effect on medical applications like the continuous HR monitoring.

Figure 21:
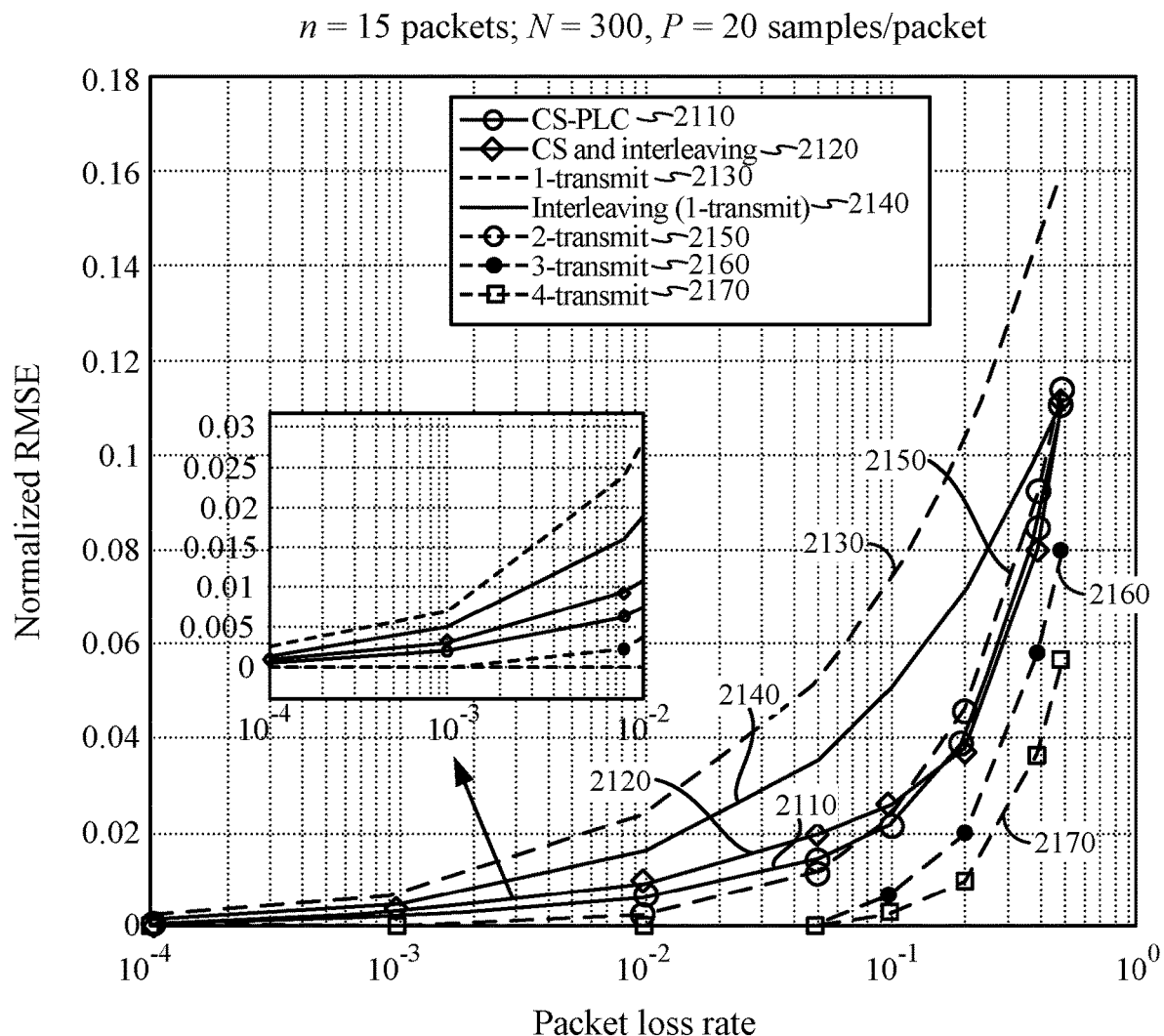
FIG. 21 illustrates a graph of example normalized RMSE performance for various PLC schemes in accordance with certain aspects of the present disclosure.

FIG. 21 illustrates comparison of the CS-PLC scheme, the CS with interleaving, and retransmission schemes. The curves 2110 and 2120 represent the CS-PLC and "CS and interleaving" schemes, respectively. The value of n is set to 15 packets. It can be noted that the reconstruction fidelity obtained using the "CS and interleaving" technique may be very comparable to the CS-PLC method. Although the precoding may be performed over smaller signal support (i.e., within each packet) in the "CS and interleaving" scheme, the interleaving process may allow to spread the information over the length of N samples. The main benefit using the "CS and interleaving" technique may be reduced precoding complexity at the sensor side, which may be typically more power-constrained side. The curve 2130 in FIG. 21 represents the 1-transmit scheme. It can be noted that at moderate packet loss rate of $10^{-2}$, 1-transmit method may perform about five times worse in terms of RMSE performance compared to the CS-PLC scheme.

The previously proposed sample-level interleaving may be employed in the 1-transmit scheme. It can be observed that with interleaving, 1-transmit method may perform only 3 times worse compared to the CS-PLC for packet loss rate of $10^{-2}$ (i.e., plot 2140 vs. plot 2110). The RMSE performance are presented for different values of k in the k-transmit approach with no interleaving. The curves 2150, 2160, and 2170 represent cases k=2, 3 and 4, respectively. It can be observed that with two and three retransmissions, significant improvement in reconstruction RMSE may be achieved. However, this may come at the cost of increased transmission bandwidth, end-to-end system latency and higher protocol complexity at the sensor.

Different PLC schemes presented above can be compared with respect to heart beat detection accuracy. This quantity can be defined as the rate of correctly identifying peaks in the ECG signal. The value of 100% may indicate a perfect beat detection, whereas the value of 0% may indicate no beat detection. According to the AAMI standards, a beat may be considered correctly detected if it lies within 150 ms of the annotated beat index available beforehand from the database.

Figure 22:
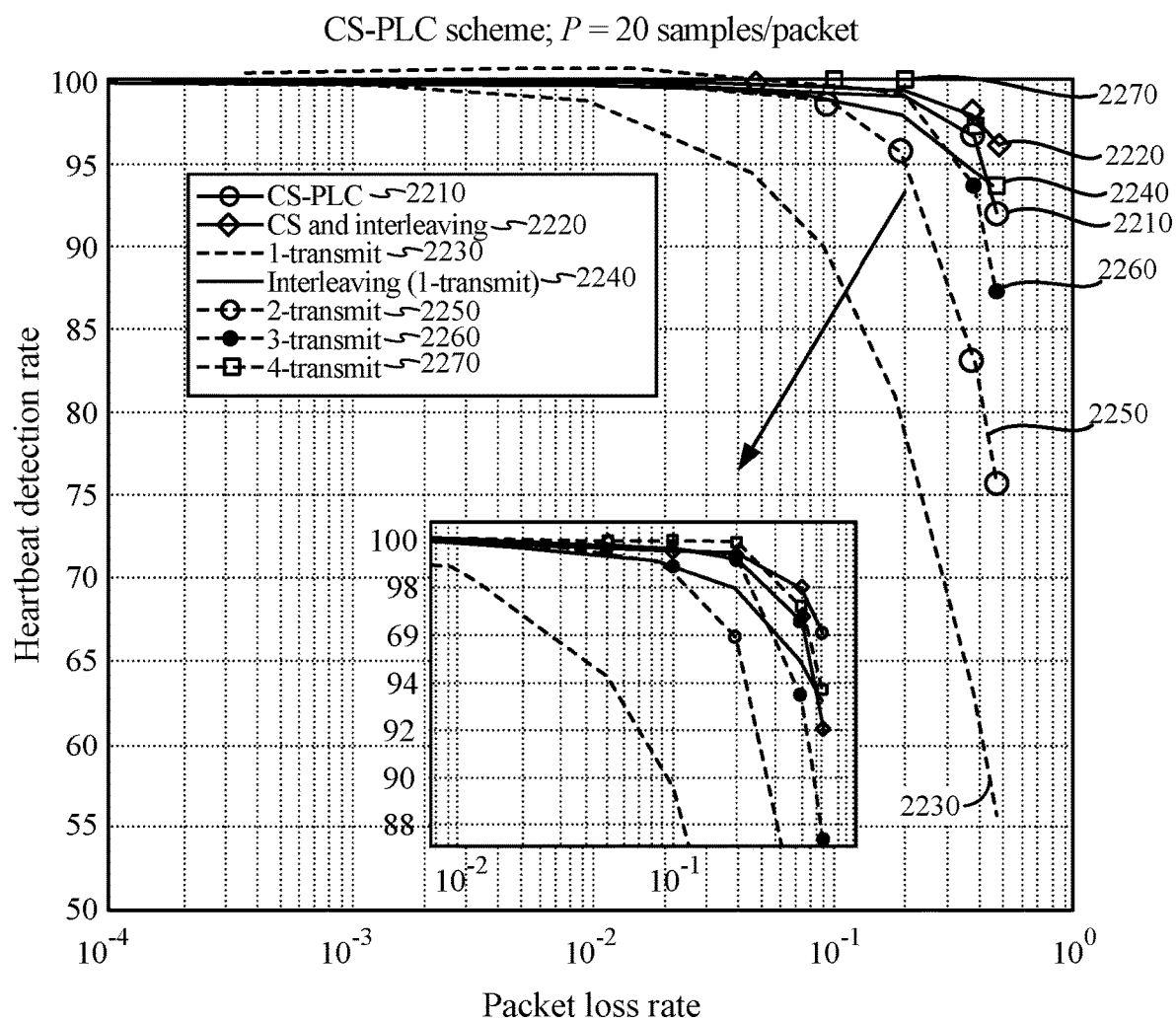
FIG. 22 illustrates heart beat detection performance comparisons for various PLC schemes in accordance with certain aspects of the present disclosure.

FIG. 22 illustrates heart beat detection performance comparisons for various PLC schemes in accordance with certain aspects of the present disclosure. The assumed parameters for Monte-Carlo simulations illustrated in FIG. 22 are the same as for the simulations illustrated in FIG. 21. There are several observations from the simulation results illustrated in FIG. 22. First, the heart beat detection rate may degrade with increasing packet loss rate as expected. Second, the performance may improve for the k-transmit schemes with increasing number of retransmissions k. Again, this may be obtainable at the expense of increased transmission bandwidth and end-to-end system latency. Third, the proposed CS-based PLC schemes (i.e., plots 2210 and 2220) may perform superior than 3-transmit method even at very high packet loss rates. It can be noted that at packet loss rate of 0.5, the CS and interleaving-based PLC method (i.e., plot 2220) may achieve 96% detection accuracy as opposed to the 3-transmit method (i.e., plot 2260), which may achieve 87% detection accuracy. With a single transmission and no interleaving (i.e., plot 2230), the detection accuracy obtained at packet loss rate of 0.5 may be equal to 55%.

Figure 23:
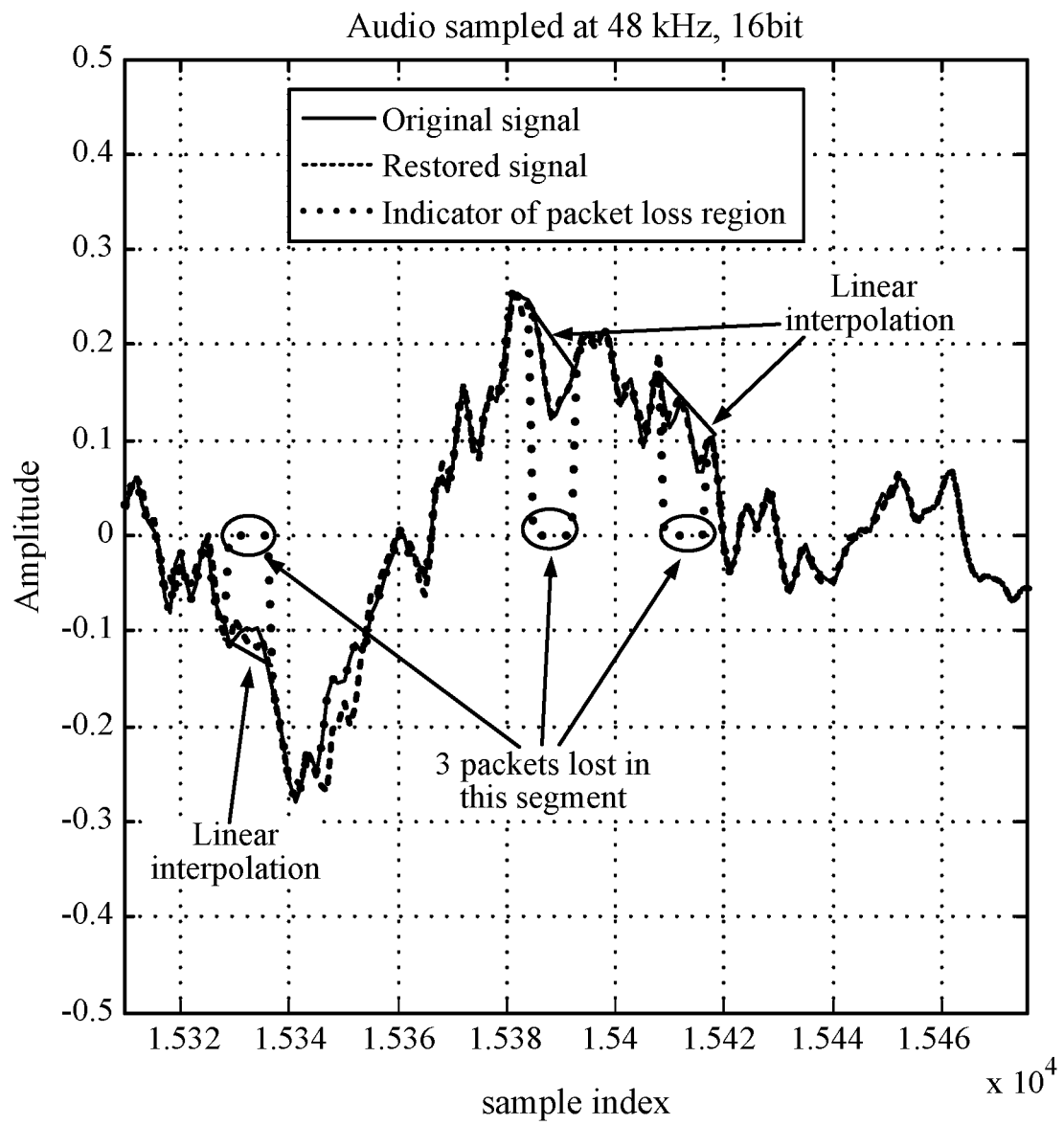
FIG. 23 illustrates an example of a restored audio signal using the CS-PLC scheme in accordance with certain aspects of the present disclosure.
Figure 24:
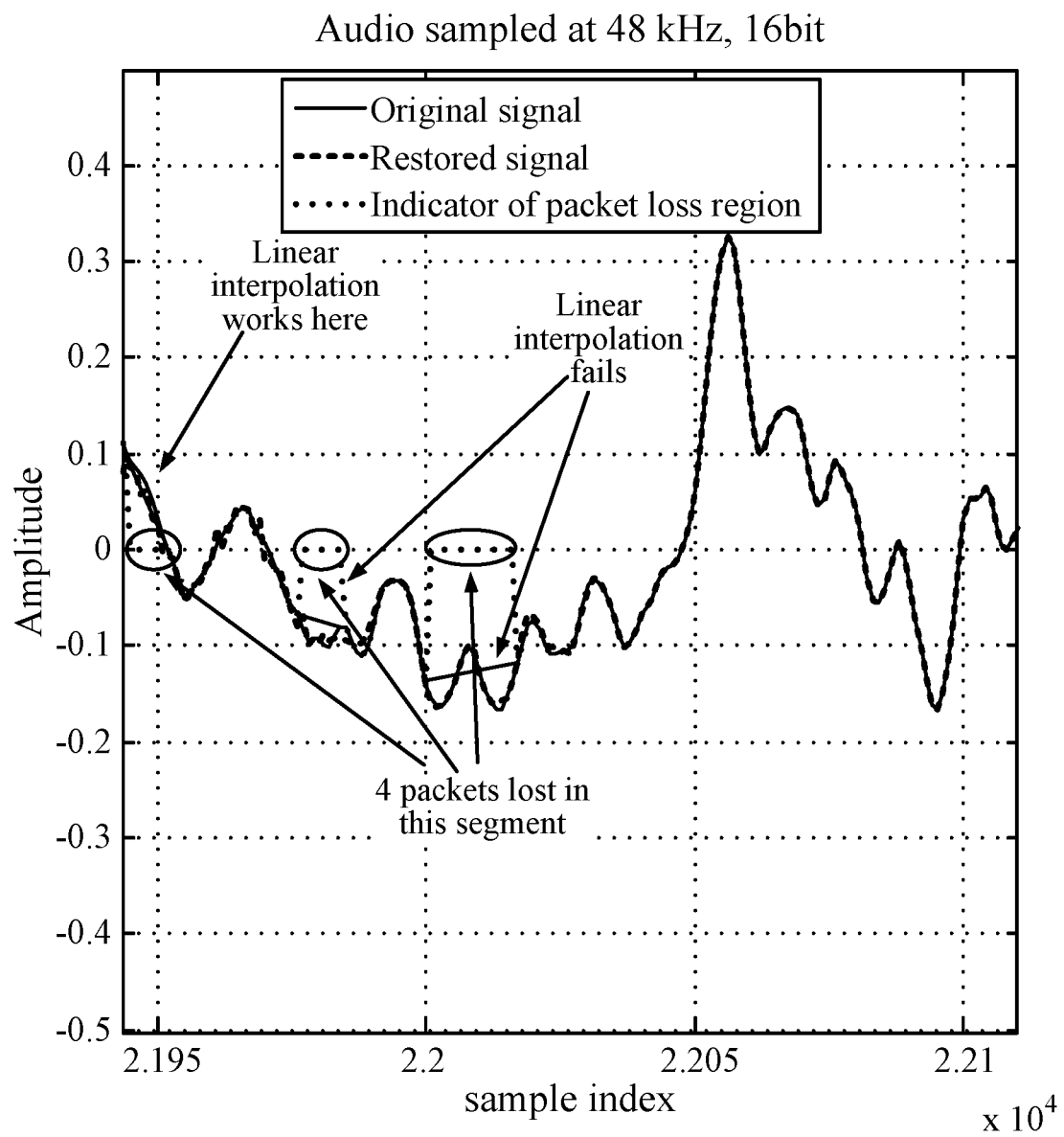
FIG. 24 illustrates another example of a restored audio signal using the CS-PLC scheme in accordance with certain aspects of the present disclosure.

FIGS. 23-24 illustrate examples of restored audio signals using the proposed CS-PLC scheme. It can be observed that the CS-PLC scheme may provide sufficiently accurate estimation results for non-biomedical signals.

To summarize, different applications of compressed sensing (CS) are proposed in the present disclosure concerning low power and robust sensors in the body area networks for healthcare and fitness applications. It is demonstrated that pulse oximeter sensor acquisition power may be significantly reduced while not compromising its utility in clinical applications. Specifically, the CS-based acquisition approach is compared with Nyquist sampling using long term data from many subjects in the MIMIC database, and it is shown that the HR and the BP estimation can meet the accepted accuracy criteria.

The CS-based approach may be used to increase the life of sensors at the cost of additional complexity at the receiver. Tradeoffs are presented between under-sampling at the sensor side and the receiver complexity for a given task. For many healthcare and fitness applications in the BAN, the receiver complexity may be well within the capabilities of current mobile handsets and PDA platforms. Applications such as heart rate estimation may not need complete reconstruction and may further reduce the receiver complexity. Finally, the benefits of the CS-based signal processing are presented for robust communication in the presence of packet losses. It is shown that the reconstruction accuracy may degrade gracefully as packet loss rate increases. It can be demonstrated that the ECG signals may be recovered with high fidelity, even in the presence of high packet loss rate conditions. Presented simulations based on the ECG data from the MIMIC database may demonstrate that up to 96% beat-detection accuracy may be maintained even at packet loss rates as high as 0.5.

The various operations of methods described above may be performed by any suitable means capable of performing the corresponding functions. The means may include various hardware and/or software component(s) and/or module(s), including, but not limited to a circuit, an application specific integrate circuit (ASIC), or processor. Generally, where there are operations illustrated in Figures, those operations may have corresponding counterpart means-plus-function components with similar numbering. For example, blocks 1610-1680, 1810-1890, 2510-2550 and 2810-2820, illustrated in FIGS. 16, 18, 25 and 28 correspond to circuit blocks 1610A-1680A, 1810A-1890A, 2510A-2550A and 2810A-2820A illustrated in FIGS. 16A, 18A, 25A and 28A.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, a plurality of DSP cores, one or more microprocessors in conjunction with one or more DSP cores, or any other such configuration.

The steps of a method or algorithm described in connection with the present disclosure may be embodied directly in hardware, in a software module executed by a processor, or in a combination of the two. A software module may reside in any form of storage medium that is known in the art. Some examples of storage media that may be used include random access memory (RAM), read only memory (ROM), flash memory, EPROM memory, EEPROM memory, registers, a hard disk, a removable disk, a CD-ROM and so forth. A software module may comprise a single instruction, or many instructions, and may be distributed over several different code segments, among different programs, and across multiple storage media. A storage medium may be coupled to a processor such that the processor can read information from, and write information to, the storage medium. In the alternative, the storage medium may be integral to the processor.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware or any combination thereof. If implemented in software, the functions may be stored as one or more instructions on a computer-readable medium. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray® disc where disks usually reproduce data magnetically, while discs reproduce data optically with lasers.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by an access terminal and/or access point as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that an access terminal and/or access point can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

A wireless device in the present disclosure may include various components that perform functions based on signals that are transmitted by or received at the wireless device. A wireless device may also refer to a wearable wireless device. In some aspects the wearable wireless device may comprise a wireless headset or a wireless watch. For example, a wireless headset may include a transducer adapted to provide audio output based on data received via a receiver. A wireless watch may include a user interface adapted to provide an indication based on data received via a receiver. A wireless sensing device may include a sensor adapted to provide data to be transmitted via a transmitter.

A wireless device may communicate via one or more wireless communication links that are based on or otherwise support any suitable wireless communication technology. For example, in some aspects a wireless device may associate with a network. In some aspects the network may comprise a personal area network (e.g., supporting a wireless coverage area on the order of 30 meters) or a body area network (e.g., supporting a wireless coverage area on the order of 10 meters) implemented using ultra-wideband technology or some other suitable technology. In some aspects the network may comprise a local area network or a wide area network. A wireless device may support or otherwise use one or more of a variety of wireless communication technologies, protocols, or standards such as, for example, CDMA, TDMA, OFDM, OFDMA, WiMAX, and Wi-Fi. Similarly, a wireless device may support or otherwise use one or more of a variety of corresponding modulation or multiplexing schemes. A wireless device may thus include appropriate components (e.g., air interfaces) to establish and communicate via one or more wireless communication links using the above or other wireless communication technologies. For example, a device may comprise a wireless transceiver with associated transmitter and receiver components (e.g., transmitter 210 or 302 and receiver 212 or 304) that may include various components (e.g., signal generators and signal processors) that facilitate communication over a wireless medium.

The teachings herein may be incorporated into (e.g., implemented within or performed by) a variety of apparatuses (e.g., devices). For example, one or more aspects taught herein may be incorporated into a phone (e.g., a cellular phone), a personal data assistant ("PDA") or so-called smartphone, an entertainment device (e.g., a portable media device, including music and video players), a headset (e.g., headphones, an earpiece, etc.), a microphone, a medical sensing device (e.g., a biometric sensor, a heart rate monitor, a pedometer, an EKG device, a smart bandage, etc.), a user I/O device (e.g., a watch, a remote control, a light switch, a keyboard, a mouse, etc.), an environment sensing device (e.g., a tire pressure monitor), a monitoring device that may receive data from the medical or environment sensing device (e.g., a desktop, a mobile computer, etc.), a point-of-care device, a hearing aid, a set-top box, or any other suitable device. The monitoring device may also have access to data from different sensing devices via connection with a network.

These devices may have different power and data requirements. In some aspects, the teachings herein may be adapted for use in low power applications (e.g., through the use of an impulse-based signaling scheme and low duty cycle modes) and may support a variety of data rates including relatively high data rates (e.g., through the use of high-bandwidth pulses).

In some aspects a wireless device may comprise an access device (e.g., an access point) for a communication system. Such an access device may provide, for example, connectivity to another network (e.g., a wide area network such as the Internet or a cellular network) via a wired or wireless communication link. Accordingly, the access device may enable another device (e.g., a wireless station) to access the other network or some other functionality. In addition, it should be appreciated that one or both of the devices may be portable or, in some cases, relatively non-portable. Also, it should be appreciated that a wireless device also may be capable of transmitting and/or receiving information in a non-wireless manner (e.g., via a wired connection) via an appropriate communication interface.

The invention claimed is:

1. A wearable system, comprising:
one or more sensors, each sensor being adapted to be worn on a body of a user and configured to capture at least one biomedical signal, wherein biomedical signals capturable by the one or more sensors include at least one of an electro-cardiogram (ECG) signal, or a photoplethysmograph (PPG) signal, or both;
the wearable system configured to:
wirelessly transmit each biomedical signal captured by the one or more sensors to a mobile phone of the user, wherein the biomedical signal is used by the mobile phone to generate a first reconstructed signal corresponding to the biomedical signal;
generate a first processed signal by processing the ECG signal or the PPG signal, or both; and
wirelessly transmit the first processed signal to the mobile phone, wherein the first processed signal is used by the mobile phone to generate a second reconstructed signal corresponding to the first processed signal and to generate an output at the mobile phone based on the second reconstructed signal, the output being provided through a user interface presented on a display of the mobile phone, wherein the wearable system is configured to adjust an under-sampling ratio based on feedback received wirelessly from another device.

2. The wearable system of claim 1, wherein the one or more sensors include a first sensor configured to generate the first processed signal, and wherein the first processed signal represents a heart rate variability, a pulse arrival time (PAT), a blood pressure, or a blood oxygen content.

3. The wearable system of claim 1, wherein the one or more sensors are configured to capture the ECG signal or the PPG signal, or both, using sampling at non-uniform time intervals.

4. The wearable system of claim 3, wherein the one or more sensors are configured to sample according to an average sampling rate $F_s$ that causes the ECG signal or the PPG signal, or both, to be under-sampled relative to a uniform sampling rate $f_s$.

5. The wearable system of claim 3, wherein the one or more sensors are configured to generate sampling instances corresponding to the non-uniform time intervals using a seed.

6. The wearable system of claim 5, wherein the seed is based on a key used in a security protocol between the one or more sensors and the mobile phone, and wherein the mobile phone is configured to, as part of reconstructing the ECG signal or the PPG signal, or both, determine the sampling instances using the key.

7. The wearable system of claim 5, wherein the wearable system is configured to communicate the seed to the mobile phone or receive the seed from the mobile phone.

8. The wearable system of claim 3, wherein the wearable system further comprises a light-emitting diode (LED), wherein the wearable system is configured to turn on the LED during sampling instances corresponding to the non-uniform time intervals, and wherein the wearable system is configured to turn off the LED between the sampling instances.

9. The wearable system of claim 1, wherein the feedback comprises an updated under-sampling ratio determined based on a comparison between a target signal and a signal derived from processing the first reconstructed signal or the second reconstructed signal.

10. A method, comprising:
capturing, by one or more sensors worn on a body of a user, at least one biomedical signal, wherein the at least one biomedical signal includes at least one of an electro-cardiogram (ECG) signal, or a photoplethysmography (PPG) signal, or both;
wirelessly transmitting each biomedical signal captured by the one or more sensors to a mobile phone of the user, wherein the biomedical signal is used at the mobile phone to generate a first reconstructed signal corresponding to the biomedical signal;
generating a first processed signal by processing the ECG signal or the PPG signal, or both;
wirelessly transmitting the first processed signal to the mobile phone, wherein the first processed signal is used by the mobile phone to generate a second reconstructed signal corresponding to the first processed signal and to generate an output based on the second reconstructed signal, the output being provided through a user interface presented on a display of the mobile phone; and
adjusting, by the one or more sensors, an under-sampling ratio based on feedback received wirelessly from another device.

11. The method of claim 10, wherein the generating of the first processed signal is performed by a first sensor of the one or more sensors, and wherein the first processed signal represents a heart rate variability, a pulse arrival time (PAT), a blood pressure, or a blood oxygen content.

12. The method of claim 10 wherein the capturing of the at least one biomedical signal comprises:
capturing the ECG signal or the PPG signal, or both, using sampling at non-uniform time intervals.

13. The method of claim 12, wherein the capturing of the at least one biomedical signal further comprises:
sampling, by the one or more sensors, according to an average sampling rate $F_s$ that causes the ECG signal or the PPG signal, or both, to be under-sampled relative to a uniform sampling rate $f_s$.

14. The method of claim 12, wherein the capturing of the at least one biomedical signal further comprises:
generating, by the one or more sensors, sampling instances corresponding to the non-uniform time intervals using a seed.

15. The method of claim 14, wherein the seed is based on a key used in a security protocol between the one or more sensors and the mobile phone, and wherein the mobile phone is configured to, as part of reconstructing the ECG signal or the PPG signal, or both, determine the sampling instances using the key.

16. The method of claim 14, further comprising:
communicating the seed to the mobile phone or receiving the seed from the mobile phone.

17. The method of claim 12, wherein the capturing of the at least one biomedical signal further comprises:
turning on a light-emitting diode (LED) during sampling instances corresponding to the non-uniform time intervals; and
turning off the LED between the sampling instances.

18. The method of claim 11, wherein the feedback comprises an updated under-sampling ratio value determined based on a comparison between a target signal and a signal derived from processing the first reconstructed signal or the second reconstructed signal.

\* \* \* \* \*